United States Patent
Gradon et al.

(10) Patent No.: US 11,129,949 B2
(45) Date of Patent: Sep. 28, 2021

(54) AUTOTITRATING METHOD AND APPARATUS

(71) Applicant: FISHER & PAYKEL HEATHCARE LIMITED, Auckland (NZ)

(72) Inventors: Lewis George Gradon, Auckland (NZ); David Robin Whiting, Auckland (NZ); Andrew Gordon Gerred, Auckland (NZ); Gregory Martyn Smith, Auckland (NZ); Fiona Elizabeth Cresswell, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 966 days.

(21) Appl. No.: 14/864,378

(22) Filed: Sep. 24, 2015

(65) Prior Publication Data
US 2016/0101250 A1    Apr. 14, 2016

Related U.S. Application Data

(63) Continuation of application No. 12/983,584, filed on Jan. 3, 2011, now Pat. No. 9,149,597, which is a
(Continued)

(51) Int. Cl.
*A61M 16/06* (2006.01)
*A61M 16/10* (2006.01)
(Continued)

(52) U.S. Cl.
CPC .... *A61M 16/0069* (2014.02); *A61M 16/0003* (2014.02); *A61M 16/024* (2017.08);
(Continued)

(58) Field of Classification Search
CPC .......... A61M 16/0069; A61M 16/0003; A61M 16/109; A61M 16/16; A61M 16/10; A61M 2205/3334
See application file for complete search history.

(56) References Cited

U.S. PATENT DOCUMENTS 3,991,304 A    11/1976 Hillsman
4,077,404 A    3/1978 Elam
(Continued)

FOREIGN PATENT DOCUMENTS

DE    33 06 607 A1    9/1983
DE    40 38 871 A1    6/1992
(Continued)

OTHER PUBLICATIONS

Ballard, Robert D. et al., "Sleep Apnea-Diagnosis and Treatment," The Western Journal of Medicine, V. 145, p. 248-250, 1986, US.
(Continued)

*Primary Examiner* — Timothy A Stanis
(74) *Attorney, Agent, or Firm* — Knobbe, Martens, Olson & Bear LLP

(57) ABSTRACT

An apparatus and method of controlling the delivery of therapeutic gas delivered to a patient undergoing positive airway pressure therapy is described. The method includes providing a flow of gas to a patient's airway at a pressure, obtaining information from the range of 0 to 25 Hz of the frequency domain of the flow, and adjusting the pressure based on the information. The apparatus includes a blower for providing a flow of gas to a patient's airway at a pressure, a sensor to measure a characteristic of the flow, a controller to obtain information from the range of 0 to 25 Hz of the frequency domain of the characteristic, and a pressure regulator for adjusting the pressure based on the information.

26 Claims, 14 Drawing Sheets

Related U.S. Application Data continuation of application No. 11/198,072, filed on Aug. 5, 2005, now Pat. No. 7,882,834.

(60) Provisional application No. 60/599,356, filed on Aug. 6, 2004.

(51) Int. Cl.
*A61M 16/00* (2006.01)
*A61M 16/16* (2006.01)

(52) U.S. Cl.
CPC .......... *A61M 16/10* (2013.01); *A61M 16/109* (2014.02); *A61M 16/16* (2013.01); *A61M 2016/003* (2013.01); *A61M 2016/0021* (2013.01); *A61M 2016/0033* (2013.01); *A61M 2205/3334* (2013.01); *A61M 2205/3372* (2013.01)

(56) References Cited

U.S. PATENT DOCUMENTS

| | | | |
|---|---|---|---|
| 4,365,636 A | 12/1982 | Barker | |
| 4,440,177 A | 4/1984 | Anderson et al. | |
| 4,444,201 A | 4/1984 | Itoh | |
| 4,448,192 A | 5/1984 | Stawitcke et al. | |
| 4,655,213 A | 4/1987 | Rapoport et al. | |
| 4,723,543 A | 2/1988 | Beran | |
| 4,957,107 A | 9/1990 | Sipin | |
| 5,076,756 A | 12/1991 | Kobayashi | |
| 5,107,831 A | 4/1992 | Halpern et al. | |
| 5,134,995 A | 8/1992 | Gruenke et al. | |
| 5,148,802 A | 9/1992 | Sanders et al. | |
| 5,199,424 A | 4/1993 | Sullivan et al. | |
| 5,203,343 A | 4/1993 | Axe et al. | |
| 5,245,995 A | 9/1993 | Sullivan et al. | |
| 5,259,373 A | 11/1993 | Gruenke et al. | |
| 5,313,937 A | 5/1994 | Zdrojkowski | |
| 5,318,038 A | 6/1994 | Jackson et al. | |
| 5,335,654 A | 8/1994 | Rapoport | |
| 5,353,788 A | 10/1994 | Miles | |
| 5,458,137 A | 10/1995 | Axe et al. | |
| 5,490,502 A | 2/1996 | Rapoport et al. | |
| 5,522,382 A | 6/1996 | Sullivan et al. | |
| 5,535,739 A | 7/1996 | Rapoport et al. | |
| 5,540,219 A | 7/1996 | Mechlenburg et al. | |
| 5,549,106 A | 8/1996 | Gruenke et al. | |
| 5,632,269 A * | 5/1997 | Zdrojkowski | A61M 16/026 128/204.21 |
| 5,645,053 A | 7/1997 | Remmers et al. | |
| 5,704,345 A | 1/1998 | Berthon-Jones | |
| 5,740,795 A | 4/1998 | Byrdon | |
| 5,928,156 A | 7/1999 | Krumbiegel et al. | |
| 5,953,713 A | 9/1999 | Behbehani et al. | |
| 6,142,952 A | 11/2000 | Behbehani et al. | |
| 6,213,119 B1 | 4/2001 | Brydon et al. | |
| 6,299,581 B1 | 10/2001 | Rapoport et al. | |
| 6,367,474 B1 | 4/2002 | Berthon-Jones et al. | |
| 6,375,621 B1 | 4/2002 | Sullivan | |
| 6,435,182 B1 | 8/2002 | Lutchen et al. | |
| 6,488,634 B1 | 12/2002 | Rapoport et al. | |
| 6,644,312 B2 | 11/2003 | Berthon-Jones et al. | |
| 6,675,797 B1 | 1/2004 | Berthon-Jones | |
| 6,739,335 B1 | 5/2004 | Rapport et al. | |
| 6,748,252 B2 | 6/2004 | Lynn et al. | |
| 6,752,151 B2 | 6/2004 | Hill | |
| 6,761,168 B1 | 7/2004 | Nadjafizadeh et al. | |
| 6,895,963 B1 | 5/2005 | Martin et al. | |
| 6,932,084 B2 | 8/2005 | Estes et al. | |
| 6,984,207 B1 | 1/2006 | Sullivan et al. | |
| 7,011,087 B1 | 3/2006 | Sullivan | |
| 2002/0124848 A1 | 9/2002 | Sullivan et al. | |
| 2003/0000528 A1 | 1/2003 | Eklund et al. | |
| 2003/0111079 A1 | 6/2003 | Matthews | |
| 2004/0123866 A1 | 7/2004 | Berthon-Jones | |
| 2004/0187870 A1 * | 9/2004 | Matthews | A61M 16/026 128/204.22 |
| 2006/0037614 A1 | 2/2006 | Madaus et al. | |

FOREIGN PATENT DOCUMENTS

| | | |
|---|---|---|
| DE | 10248590 A1 | 4/2004 |
| EP | 0 046 570 A2 | 3/1982 |
| EP | 0 920 845 B1 | 4/2004 |
| WO | WO 88/10108 A1 | 12/1988 |
| WO | WO 89/10768 A1 | 11/1989 |
| WO | WO 90/14121 A1 | 11/1990 |
| WO | WO90/14121 A1 | 11/1990 |
| WO | WO 01/05460 A1 | 1/2001 |
| WO | WO 2004/047621 A2 | 6/2004 |

OTHER PUBLICATIONS

Canadian Office Action dated Oct. 31, 2012 for Application No. 2,576,171 in 3 pages.

Canadian Examination Report for Canadian Application No. 2,576,171 dated Sep. 18, 2013 in 3 pages.

Cohen, Arnon, "Biomedical Signal Processing," Volume TI Compression and Automatic Recognition, p. 1-18, CRC Press, Inc., US 1986.

Dupuis, Yvon, "Ventilators Theory and Clinical Application," p. 107-117, C.V. Mosby Company, 1986, US.

English translation of DE 102 48 590 A1, Madaus et al, Method and device for carrying out a signal-processing viewing of a measurement signal that is correlated to the respiratory activity of an individual, Apr. 29, 2004.

Garay, Stuart M., "Therapeutics Options for Obstructive Sleep Apnea," Respiratory Management, Jul./Aug. 1987, US.

Guilleminault, C. et al., "Unattended CPAP Titration: Toward a Smart Machine," Sleep Research, V. 21, p. 342, 1992. US.

India Examination Report dated Feb. 11, 2013 for Application No. 653/KOLNP/2007 in 2 pages.

J.E. Remmers et al., "Mechanics of the Pharynx in Patients with Obstructive Sleep Apnea," Sleep and Respiration, p. 261-271, 1990.

Lafortuna, Claudio L. et al.; "Inspiratory Flow Pattern in Humans"; The American Physiological Society; p. 1111-1119; 1984; USA.

Miles, L.E. et al. "Development and Application of Automatic Nasal CPAP Calibration Procedures for Use in the Unsupervised Home Environment," Sleep, V.16, p. S118-S119, 1993, US.

Miles, L.E. et al., "Development and Application of an Automatic Nasal CPAP Calibration Procedure for Use in the Unsupervised Home Environment," Sleep Research, V.21, p. 352, 1992.

Miles, L.E. et al., "Different Roles for an Automatic Nasal CPAP Calibration Procedure and 'Smart-PAP'," Sleep Research, V. 22 p. 238, 1993, US.

Minetti, A.E. et al.; "Respiratory Airflow Pattern in Patients with Chronic Airway Obstruction"; Clinical Physiology; vol. 7 p. 283-296; USA.

Rapoport, David M et al., "Reversal of the 'Pickwickian Syndrome' by Long-Term Use of Nocturnal Nasal-Airway Pressure," New England Journal of Medicine, v.307, p. 931-33, 1982.

Rapoport, David M., "Techniques for Administering Nasal CPAP," Respiratory Management, Jul./Aug. 1987, US.

Schwartz, Alan et al., "Induction of Upper Airway Occlusion in Sleeping Individuals with Subatmospheric Nasal Pressure," Journal of Applied Physiology, V. 64(2), p. 53-542, 1988.

Southworth, Raymond et al., "Digital Computation and Numerical Methods," p. 6-10, McGraw Hill Book Company, 1965, US.

Sullivan, Colin et al., "Reversal of Obstructive Sleep Apnea by Continuous Positive Airway Pressure Applied Through the Nares," The Lancet, p. 862-865, 1981.

Willard, Hobart et al., "Instrumental Methods of Analysis," Sixth Edition, p. 897-930, D. Van Nostrand Company, 1981, US.

Supplementary Partial European Search Report for European Application No. EP 05 77 6748 dated May 2, 2017 in 4 pages.

(56) References Cited

OTHER PUBLICATIONS

Miles, L.E. et al. "Development and Application of Automatic Nasal CPAP Calibration Procedures for Use in the Unsupervised Home Environment," Sleep, V.16, p. 5118-S119, 1993, US.
Examination Report issued in Canadian Application No. 3,065,994 dated Mar. 9, 2021.
Examination Report issued in Canadian Application No. 3,914,743 dated Sep. 2, 2020.

* cited by examiner

AUTOTITRATING METHOD AND APPARATUS

CROSS REFERENCE TO RELATED APPLICATION

This application is a continuation of U.S. patent application Ser. No. 12/983,584, filed Jan. 3, 2011, which is a continuation of U.S. patent application Ser. No. 11/198,072, filed Aug. 5, 2005 and issued as U.S. Pat. No. 7,882,834, which claims the benefit of U.S. provisional patent application Ser. No. 60/599,356, filed on Aug. 6, 2004. The disclosure of each of these prior applications is incorporated herein by reference in its entirety.

FIELD

This invention is generally directed to a method and apparatus for controlling the positive air pressure applied to a patient undergoing positive airway pressure therapy.

BACKGROUND

Obstructions in some patients' airways during sleep can cause limited airflow, leading to apnea, hypopnea, or snoring. The obstruction is often a collapsed pharynx. The obstruction may be a partial airway obstruction, leading to altered characteristics of the airflow. A hyperpnoea is a reduction of flow that is greater than fifty percent, but not complete. An apnea, however, is a complete cessation of airflow. Each of these conditions frequently leads to sleep deprivation.

It is well known to treat patients suffering from sleep deprivation with positive airway pressure therapy ("PAP"). This therapy can be Continuous Positive Airway Pressure ("CPAP"), Variable Positive Airway Pressure ("VPAP"), Bi-level Positive Airway Pressure ("BiPAP"), or any of numerous other forms of respiratory therapy. The application of positive pressure to the patient's pharynx helps minimize or prevent this collapse. Positive airway pressure therapy is currently applied by means of an apparatus containing a pressure source, typically a blower, through a tube to a mask, which the patient wears in bed.

It is desired to control the applied pressure. Too little pressure tends not to solve the problem. Too much pressure tends to cause discomfort to the patient, such as drying out of the mouth and pharynx, as well as difficulty in exhaling against the applied pressure. The difficulty in applying optimum pressure is that incidents of airway obstruction come and go through the course of a night's sleep. One solution is to try to find an optimum pressure for a particular patient and maintain that pressure. This method requires the patient's stay at a sleep clinic, where sleep specialists can monitor the patient's course of breathing throughout one or more night's sleep, prescribe the appropriate pressure for that patient, and then set the apparatus to deliver the appropriate pressure. This method is, of course, inconvenient as well as expensive to the patient and tends to be inaccurate, as a typical patient will not sleep the same when away from familiar bedding and surroundings.

Accordingly, it is desirable to be able to adjust the applied pressure without requiring the patient to attend at a sleep center. Various methods of in-home adjustments have been considered. One method generally thought to be effective is to monitor the patient to try to anticipate the onset of an obstructed airway, and to adjust the pressure in response. When an elevated upper airway resistance or flow obstruction is anticipated or underway, the apparatus increases the applied pressure. When the patient returns to normal sleep, the applied pressure is reduced. The problem then, is to determine when a flow obstruction is occurring or is about to occur. It is desired to anticipate correctly in order to avoid the problems set forth above for when too much or too little pressure is applied.

Various methods have been proposed to solve this problem. In U.S. Pat. No. 5,107,831 to Halpern, an apparatus monitors the airflow to the patient and posits an event of airway obstruction when the patient's breath fails to meet a predetermined threshold of flow rate or duration. In U.S. Pat. No. 5,1345,995 to Gruenke, an apparatus monitors the airflow to the patient and analyzes the shape of the flow versus time waveform. If the shape of this waveform tends to be flattened, that is, more similar to a plateau than to a sinusoid, the apparatus posits an event of airway obstruction. In U.S. Pat. No. 5,245,995 to Sullivan, an apparatus monitors the patient's sound with a microphone. If audible snores are detected, the apparatus posits an event of airway obstruction. Similarly, in U.S. Pat. No. 5,953,713 to Behbehani, an apparatus measures the total pressure within an interface placed over a patient's airway and inputs frequency data in the range 100 to 150 Hz into a neural network to determine the presence of a pharyngeal wall vibration (a snore) which, according to Behbehani, is a precursor to sleep disorder breathing.

These methods have not proven totally satisfactory in controlling the applied pressure during PAP therapy. For example, the '713 patent, by measuring in the range of 100 to 150 Hz, essentially tests for snoring and does not measure or analyze any information concerning partial airway obstruction (as described within the present application), as this information is found in the lower frequency range 0 to 25 Hz. FIGS. 1 and 2 are plots in the frequency domain of energy v. frequency of typical breathing. As can be seen, there is a marked difference between normal breathing and breathing characterized by a partial airway obstruction, all in low frequencies. The present application exploits this difference to control the delivery of therapeutic gas.

Moreover, the methods of the prior art are unsatisfactory in analyzing a signal in a high-noise environment. The inventors herein have discovered an alternate way to detect the onset of an event of airway obstruction and to control the applied pressure from a high-noise signal such as results from a person's breathing over the course of a night. Accordingly, the method and apparatus of the present invention fulfill the need for analyzing a signal from a patient in order to control the applied pressure during PAP therapy.

SUMMARY

The present invention in one embodiment is a method of controlling positive airway pressure therapy by providing a flow of gas to a patient's airway at a pressure, obtaining information from the frequency range of zero to 25 HZ in the frequency domain of the flow, and adjusting the pressure based on the information. In another embodiment, the present invention is an apparatus for providing controlled positive airway pressure therapy, having a blower for providing a flow of gas to a patient's airway, a sensor to measure a characteristic of the flow, a controller to obtain information from the frequency range of zero to 25 HZ in the frequency domain of the characteristic, and a pressure regulator for adjusting the pressure based on the information.

BRIEF DESCRIPTION OF THE DRAWINGS

The organization and manner of the structure and operation of the invention, together with further objects and advantages thereof, may best be understood by reference to the following description, taken in connection with the accompanying drawings, wherein like reference numerals identify like elements in which.

DETAILED DESCRIPTION OF THE INVENTION

Figure 1:
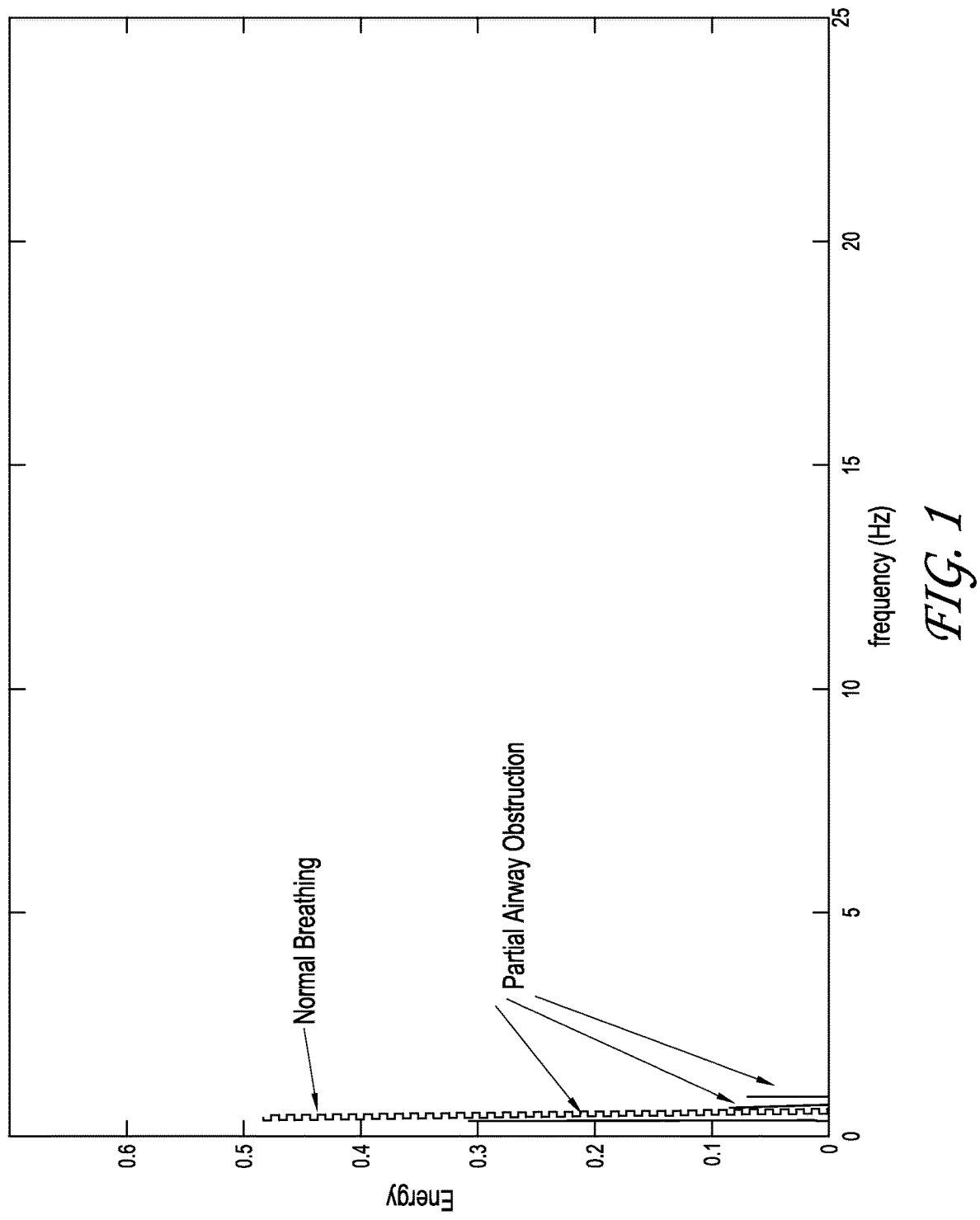
FIG. 1 is a plot in the frequency domain of energy v. frequency for normal breathing and breathing characterized by partial airway obstruction.

While the invention may be susceptible to embodiment in different forms, there is shown in the drawings, and herein will be described in detail, a specific embodiment with the understanding that the present disclosure is to be considered an exemplification of the principles of the invention, and is not intended to limit the invention to that as illustrated and described herein.

Figure 3:
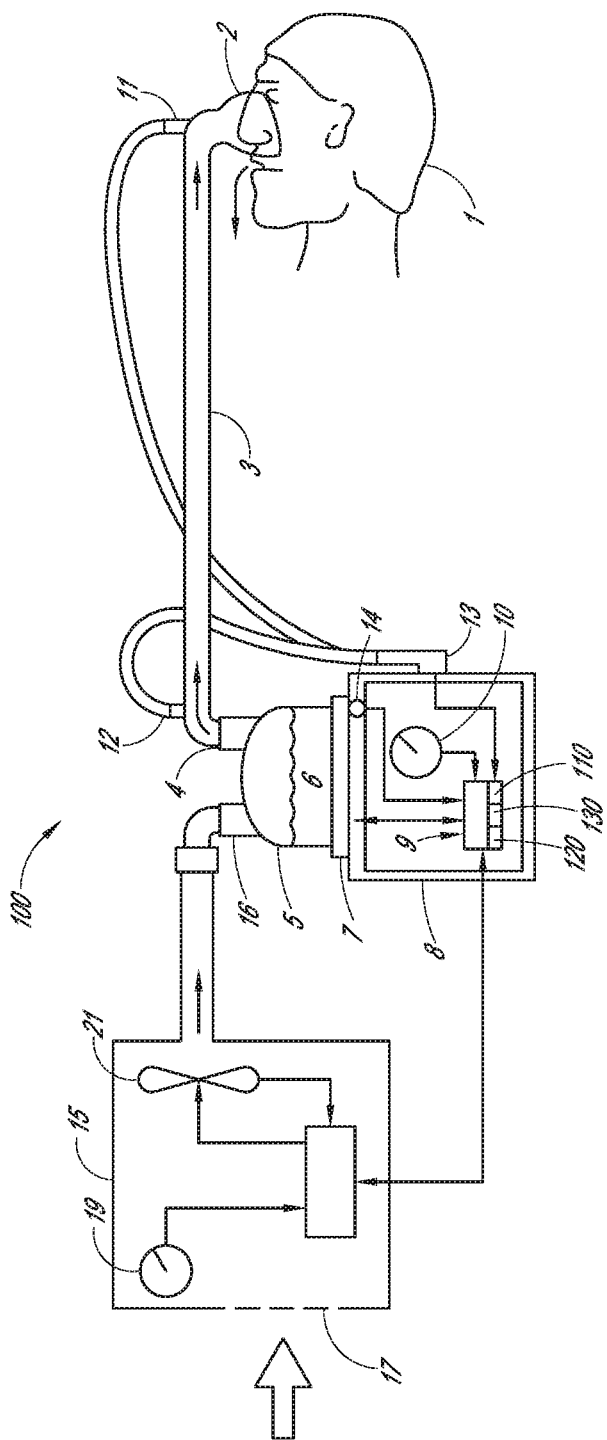
FIG. 3 is a diagram of an exemplary positive airway pressure apparatus of the preferred embodiment of the present invention.

A positive airway pressure apparatus 100 of the preferred embodiment of the present invention is shown in FIG. 3 in which the patient 1 receives humidified, pressurized gas through an inspiratory conduit 3. It should be understood that the delivery systems could be CPAP (Continuous Positive Airway Pressure), VPAP (Variable Positive Airway Pressure), BiPAP (Bi-level Positive Airway Pressure), or any of numerous other forms of respiratory therapy. The apparatus 100 and method 200 of the present invention will be described as used for CPAP but an artisan of ordinary skill in the art will readily adapt both for use with VPAP, BiPAP, or another positive airway pressure therapeutic system.

Inspiratory conduit 3 is attached at one end to a mask 2, preferably one such as is described in U.S. Pat. No. 6,662, 803. Inspiratory conduit 3 connects at its other end to the outlet 4 of a humidification chamber 5, which contains a volume of water 6. Inspiratory conduit 3 may contain heating heater wires (not shown) or other suitable heating elements that heat the walls of the conduit to reduce condensation of humidified gases within the conduit. Humidification chamber 6 is preferably formed from a plastic material and may have a highly heat-conductive base (for example an aluminum base) that is in direct contact with a heater plate 7 of humidifier 8.

Electronic controller 9 controls the various components of the apparatus 100. Controller 9 may be a microprocessor-based controller containing, as is well known in the art, RAM, ROM, an ALU, one or more registers, a data bus, counters (including at least a breath number counter 120 and a pressure decrease counter 130), and one or more buffers (including at least a circular buffer 110). Controller 9 executes computer software commands stored in its RAM and ROM.

Controller 9 receives input from sources such as user input dial 10 through which a user of the device may, for example, set a predetermined required value (preset value) of various characteristics of the gases supplied to the patient 1, such as initial airflow, pressure, humidity, or temperature of the gases. Controller 9 preferably receives input relating to airflow from differential pressure sensor 11, which is preferably located in blower 15. Differential pressure sensor 11 could alternatively be located elsewhere, upstream of mask 2, such as within conduit 3 or anywhere on mask 2. Alternatively, controller 9 may receive input related to airflow by direct measurement of flow at any point from blower 15 to mask 2. Controller 9 may also receive input from other sources, for example temperature sensors 12 through connector 13 and heater-plate temperature sensor 14.

In response to the user-set inputs and the other inputs, controller 9 determines when (or to what level) to energize heater plate 7 to heat the water 6 within humidification chamber 5. As the volume of water 6 within humidification chamber 5 is heated, water vapor begins to fill the volume of the chamber 5 above the water's surface and is passed out of the outlet 4 of humidification chamber 5 with the flow of gases (for example air) provided from a gas supply device such as blower 15, which gases enter the chamber 5 through inlet 16. Exhaled gases from the patient 1 are passed directly to ambient surroundings in FIG. 3.

Blower 15 is provided with a variable-pressure regulating device such as variable speed fan 21, which draws air or other gases through blower inlet 17. The speed of variable speed fan 21 is controlled by electronic controller 9 in response to inputs from the various components of apparatus 100 and by a user-set predetermined required value (preset value) of pressure or fan speed via dial 19.

Controller 9 is programmed with five algorithms:
1. Breath Detection Algorithm;
2. Apnea Detection Algorithm;
3. Hypopnea Detection Algorithm;
4. Partial Airway Obstruction Detection Algorithm; and
5. Pressure Adjusting Algorithm.

Figure 4:
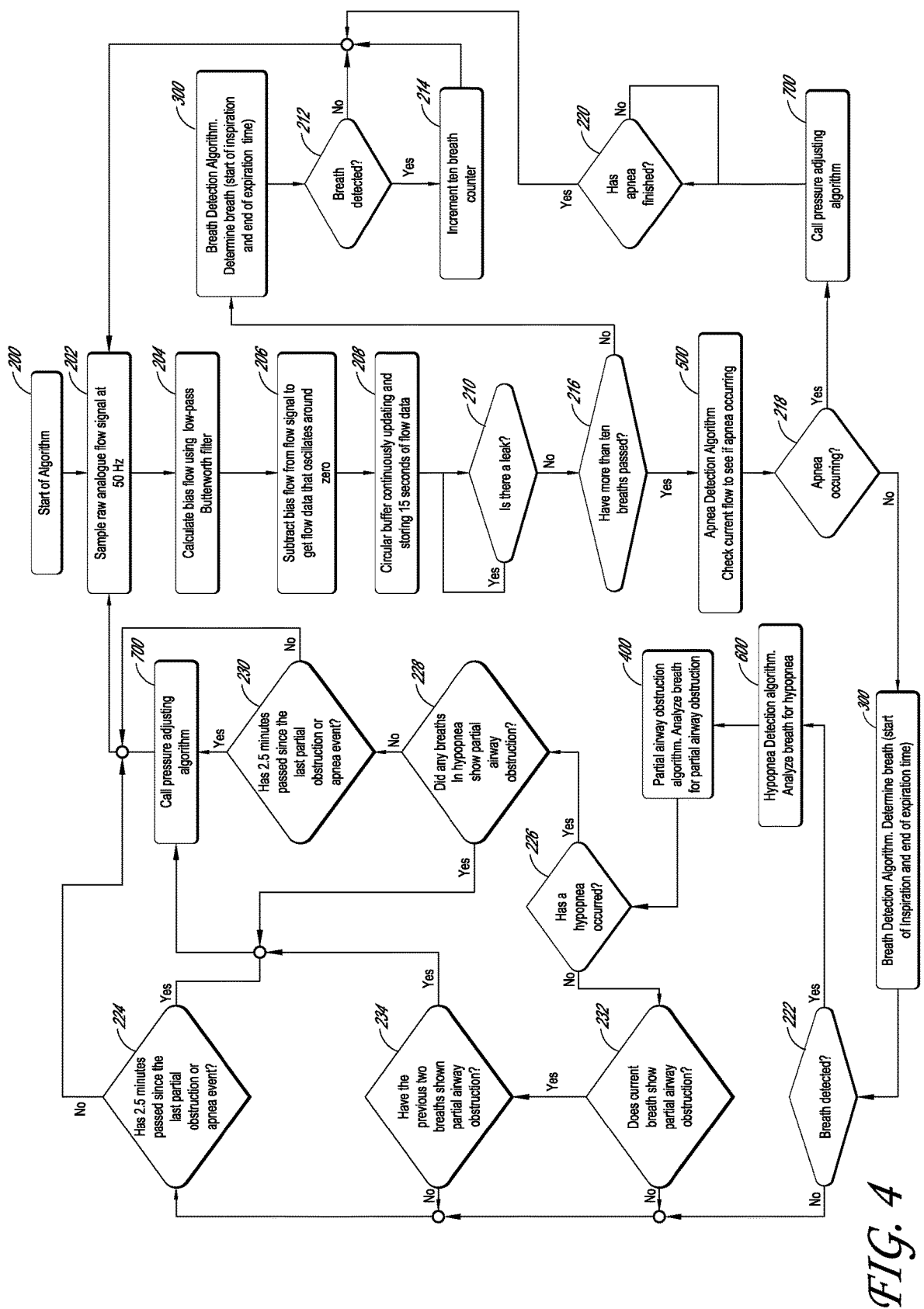
FIG. 4 is a block diagram of the main algorithm of the method of the preferred embodiment of the present invention, showing the interaction of the five algorithms.

These algorithms interact as diagramed in FIG. 4. When the patient 1 turns on the apparatus 100, the controller 9 receives data from pressure sensor 11 and starts the main algorithm (step 200). Pressure sensor 11 is preferably a differential pressure sensor, and controller 9 converts differential pressure data to airflow data. Controller 9 samples the raw analogue flow signal at 50 Hz (step 202) and calculates bias flow (step 204). Bias flow, such as occurs from leaks in the mask 2 or elsewhere in the apparatus 100, is obtained preferably via a Butterworth low-pass filter (with a rise time of approximately thirty seconds). The information stored in circular buffer 110 in controller 9 is therefore net airflow data, as the controller 9 removes the bias flow (step 206). Circular buffer 110 in controller 9 is continuously updating data and storing that data for 15 seconds (step 208).

Accordingly, throughout these algorithms, the flow being analyzed does not contain the bias flow. That is, the flow oscillates about zero flow.

The incoming flow data is continuously checked for the presence of a leak (step 210). If a significant leak is detected the algorithm is paused until the leak is resolved.

If there are no leaks and fewer than ten breaths have passed, the current data is analyzed by the Breath Detection Algorithm (step 300), as will be described in connection with FIG. 5. The Breath Detection Algorithm determines where the oldest breath begins and ends.

If no breath is detected (step 212), the main algorithm starts over with sampling the raw analogue flow signal (step 202). If a breath is detected (step 212), a breath number counter 120 is incremented (step 214), and the main algorithm starts over with sampling the raw signal (step 202).

Since it is assumed that the patient 1 will breathe a minimum of ten breaths before any apneas or hypopneas occur, the main algorithm of the preferred embodiment counts to determine if at least ten breaths have occurred (step 216). If more than ten breaths have occurred, the apparatus proceeds to the Apnea Detection Algorithm (step 500), as will hereinafter be described in connection with FIG. 7. If fewer than ten breaths have occurred, circular buffer 110 in controller 9 continues to sample raw analogue data (step 202).

Once ten breaths have occurred, the main algorithm proceeds as diagramed in FIG. 4. The Apnea Detection Algorithm (step 500) constantly checks the real-time incoming flow to see if an apnea is occurring (step 218), as will be described in greater detail in connection with FIG. 7. If an apnea is occurring, the Pressure Adjusting Algorithm (step 700) is called, as will be described in connection with FIG. 9. Once the apnea has finished (step 220), the main algorithm starts over with sampling raw data (step 202). If no apnea is occurring, the Breath Detection Algorithm (step 300) is called.

If no new breath has been detected (step 222), the algorithm checks to see if 2.5 minutes have passed since the last partial obstruction or apnea event (step 224). If not, the main algorithm starts over with sampling raw data (step 202). If so, the Pressure Adjusting Algorithm (step 700) is called. If a breath is detected, the Hypopnea Detection Algorithm is called (step 600), as will be described in connection with FIG. 8, followed by the Partial Airway Obstruction Algorithm (step 400) as will be explained in connection with FIG. 6.

The Hypopnea Detection Algorithm (step 600) checks to see if a breath is possibly part of a hypopnea. The Partial Airway Obstruction Algorithm (step 400) is called to check for partial airway obstruction (step 232). If the Hypopnea Detection Algorithm finds that a hypopnea has occurred (step 226), the main algorithm checks to see if any breaths in the hypopnea showed partial airway obstruction (step 228). If so, the Pressure Adjusting Algorithm is called (step 700). If not, the main algorithm checks to see if 2.5 minutes have passed since the last partial obstruction or apnea event (step 230). If so, the Pressure Adjusting Algorithm is called (step 700). If not, the main algorithm starts over with sampling raw data (step 202).

The Partial Airway Obstruction Algorithm checks for partial airway obstruction (step 232) in the event a hypopnea has not occurred. If the current breath shows a partial airway obstruction, the main algorithm checks to see if the previous two breaths have shown a partial airway obstruction (step 234). If so, the Pressure Adjusting Algorithm (step 700) is called. If the current breath does not show a partial airway obstruction (step 232) or if the previous two breaths do not show a partial airway obstruction (step 234), the main algorithm checks to see if 2.5 minutes have passed since the last partial obstruction or apnea event (step 224). If so, the Pressure Adjusting Algorithm (step 700) is called; if not, the main algorithm starts over with sampling raw data.

Using the above algorithms, the applied positive airway pressure is at the lowest pressure required by the patient 1 to achieve therapeutic treatment. The details of the algorithms will now be explained.

Breath Detection Algorithm

Figure 5:
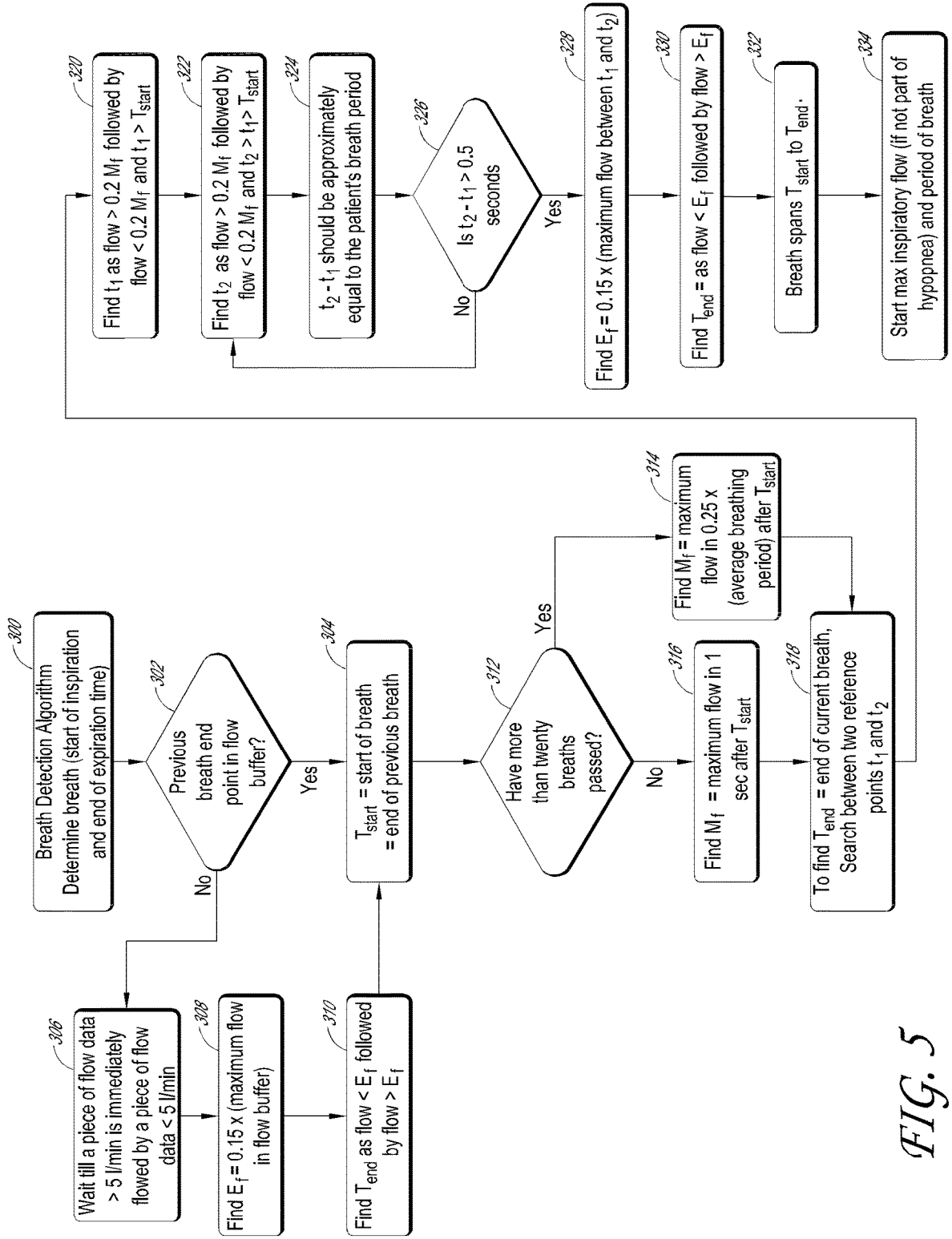
FIG. 5 is a block diagram of the Breath Detection Algorithm of the preferred embodiment of the present invention.

Two routines are used, as diagramed in FIG. 5, depending on how many breaths have been detected since the program was initiated. The two routines differ, in that one incorporates the breathing period of the patient 1.

The Breath Detection Algorithm (step 300) initially determines if a previous breath's end is still contained within the flow buffer (step 302). If a previous breath's end point is still in the flow buffer, the start of the next breath (beginning of inspiration, or $T_{start}$) will be the data point following the end point of the previous breath (step 304). If the previous breath's end point is not in the buffer (such as if an apnea occurred), the new end point is determined, once a piece of flow data greater than five liters per minute is immediately followed by a piece of flow data less than 5 liters per minute has occurred (step 306), by searching the flow buffer to find $E_f$ where $E_f$ is 0.15 times the maximum flow in the buffer (step 308), and where flow is increasing, that is, flow is less than $E_f$ followed by flow greater than $E_f$ (step 310). The new end point $T_{end}$ is then set as the start of the next breath (step 304).

At this point, the algorithm determines whether more than twenty breaths have occurred (step 312). If so, the algorithm searches to find $M_f$, the maximum flow over the last one-quarter of the average breathing period after $T_{start}$ (step 314). If twenty or fewer breaths have occurred, $M_f$ is defined as the maximum flow in the next second after $T_{start}$ (step 316).

Figure 10:
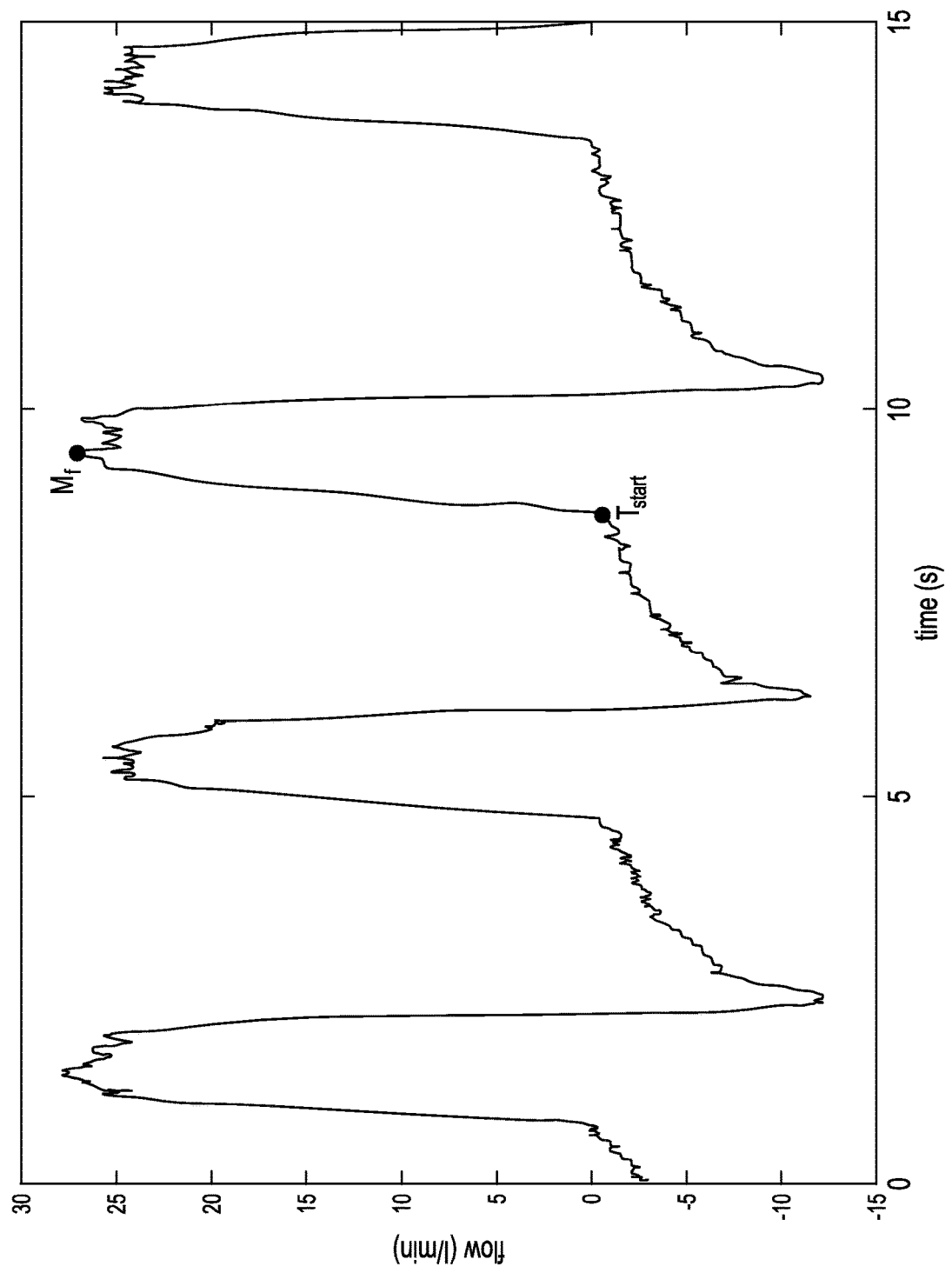
FIG. 10 is a diagram of airflow versus time, illustrating $T_{start}$ and $M_f$.

The end point of expiration, $T_{end}$, is determined by searching between two reference points (step 318) (reference points $t_1$, $t_2$ are shown in FIG. 10, a plot of airflow to the patient, as determined from differential pressure sensor 11, versus time). Each reference point $t_1$, $t_2$ is identified by determining the occurrence of a flow data value greater than the reference value followed by a flow data value less than the reference value (steps 320, 322), where $t_2$ is after $t_1$, which is after $T_{start}$.

The reference value is given by:

$$\text{reference value} = 0.2 \times M_f$$

where $M_f$ is the maximum flow in 0.25×average breathing period since the beginning of inspiration (as found in step 314).

$M_f$ is illustrated in FIG. 10, also a plot of airflow to the patient 1, as determined from differential pressure sensor 11, versus time.

The period between $t_1$ and $t_2$ should be greater than 0.5 sec (step 326). If not, $t_2$ is found again (step 322). The maximum flow, greater than zero, between the two reference points $t_1$, $t_2$ is calculated and used to determine the end of expiration $E_f$ (step 328). The end of expiration is:

$$E_f = 0.15 \times M_{t1-t2}$$

where $$M_{t1-t2} = \text{maximum flow between } t_1 \text{ and } t_2$$

Figure 11:
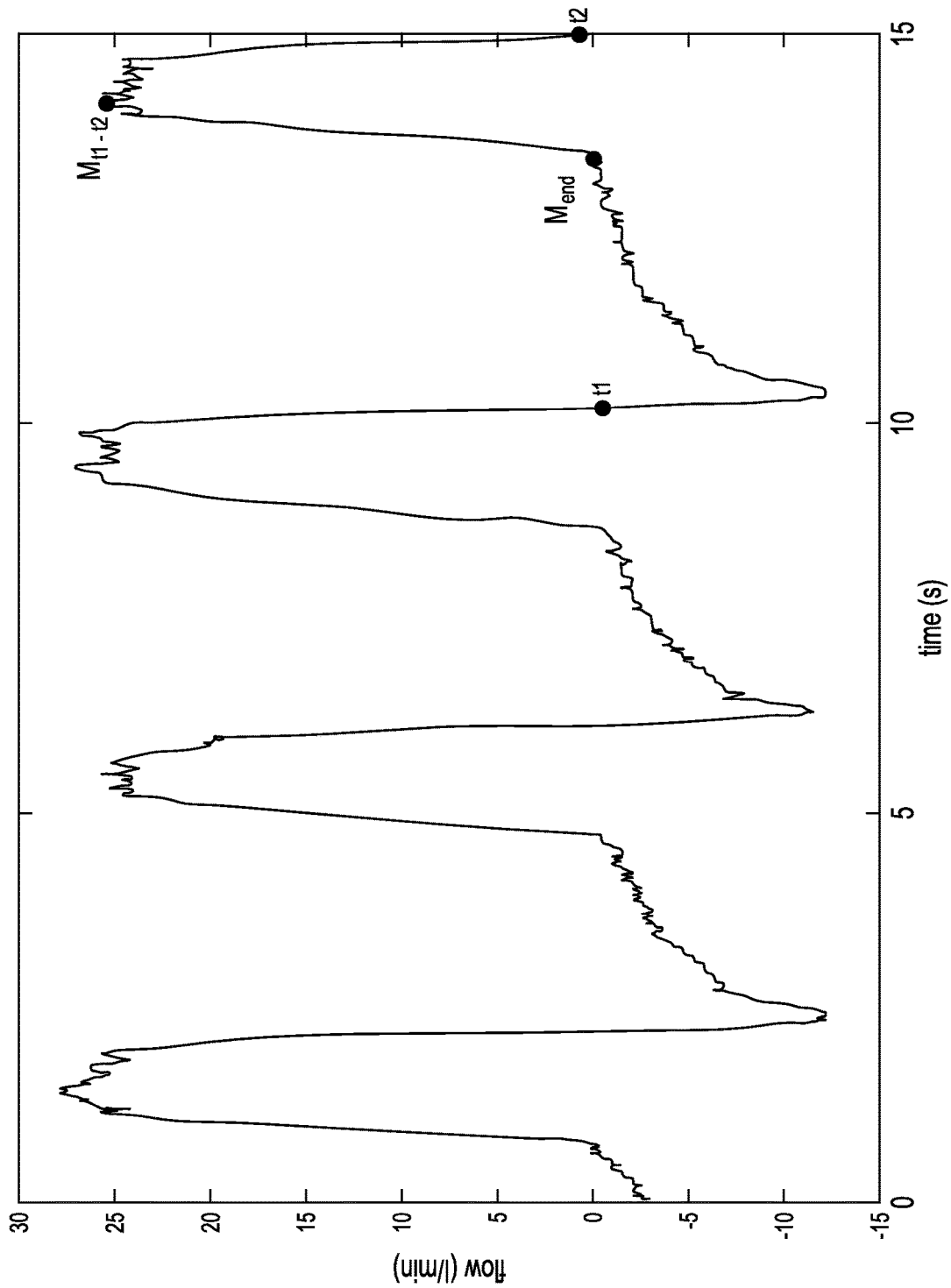
FIG. 11 is a diagram of airflow versus time, illustrating $T_{end}$, $t_1$, $t_2$ and $M_{t1-t2}$.

$M_{t1-t2}$, $t_1$, and $t_2$ are illustrated in FIG. 11.

A flow data value less than $E_f$ immediately followed by a flow data value greater than $E_f$ indicates the end of the breath $T_{end}$ (step 330). The breath is therefore from $T_{start}$ to $T_{end}$ (step 332). The apparatus then stores the maximum flow $M_{t1-t2}$, provided the breath is not part of a hypopnea, as determined by the Hypopnea Detection Algorithm (step 600), as will be hereinafter described, and stores the period of the breath (step 334).

The period of the breath and the maximum inspiratory flow are used by the Apnea Detection Algorithm (step 500) and the Hypopnea Detection Algorithm (step 600), as will be described.

Partial Airway Obstruction Algorithm

Figure 6:
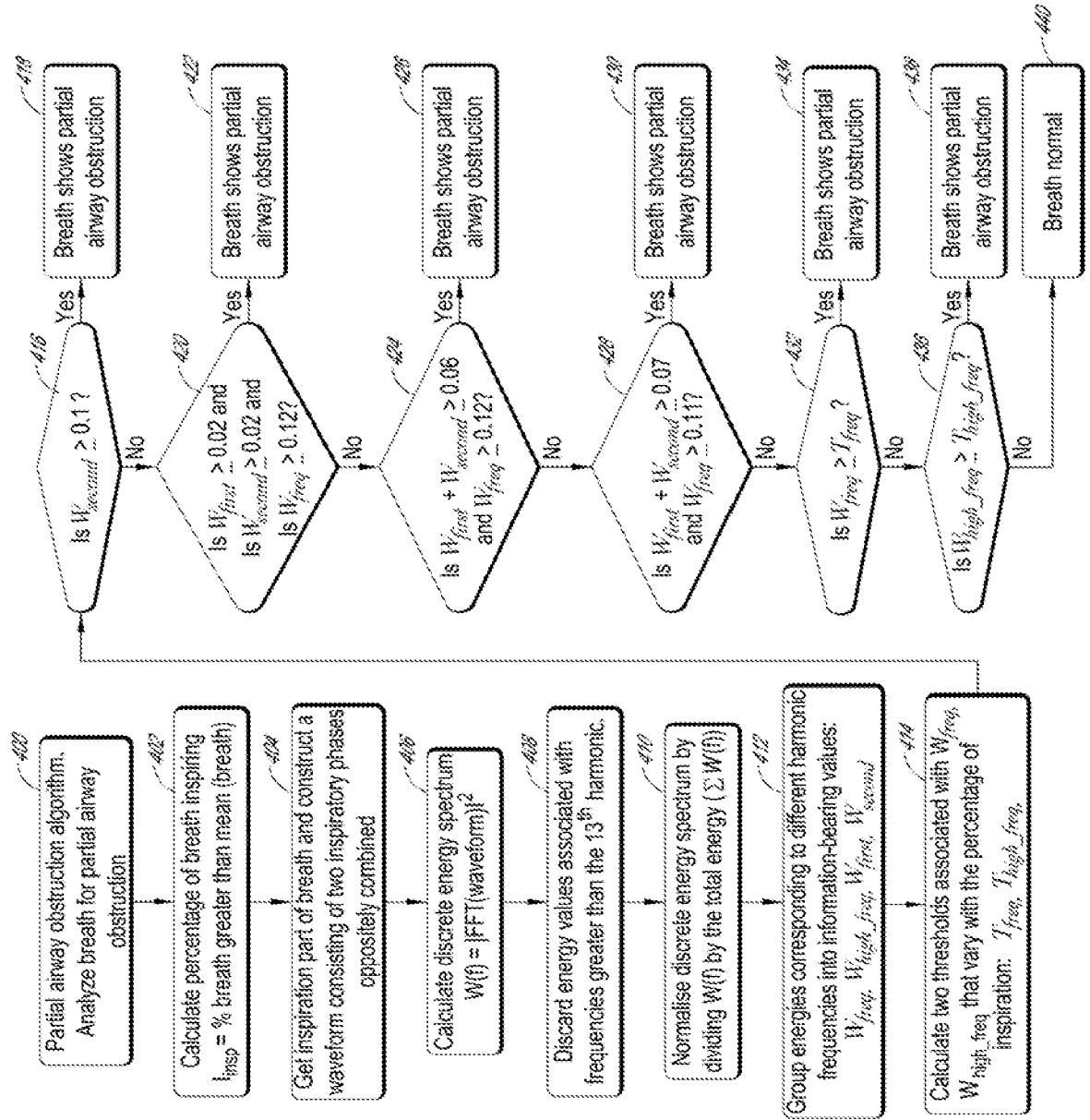
FIG. 6 is a block diagram of the Partial Airway Obstruction Algorithm of the preferred embodiment of the present invention.

The Partial Airway Obstruction Detection Algorithm (step 400) is diagramed in FIG. 6. It analyzes a breath, previously detected by the Breath Detection Algorithm (step 300), for the presence of a partial airway obstruction (partial obstruction of the upper airway).

When the patient 1 breathes, pressure gradients are generated between the lungs and atmosphere. The physiology of the upper airway combined with these pressure gradients and Bernoulli's Effect can result in partial collapse of the upper airway during inspiration. This partial collapse is prevalent in people with obstructive sleep apnea.

Figure 2:
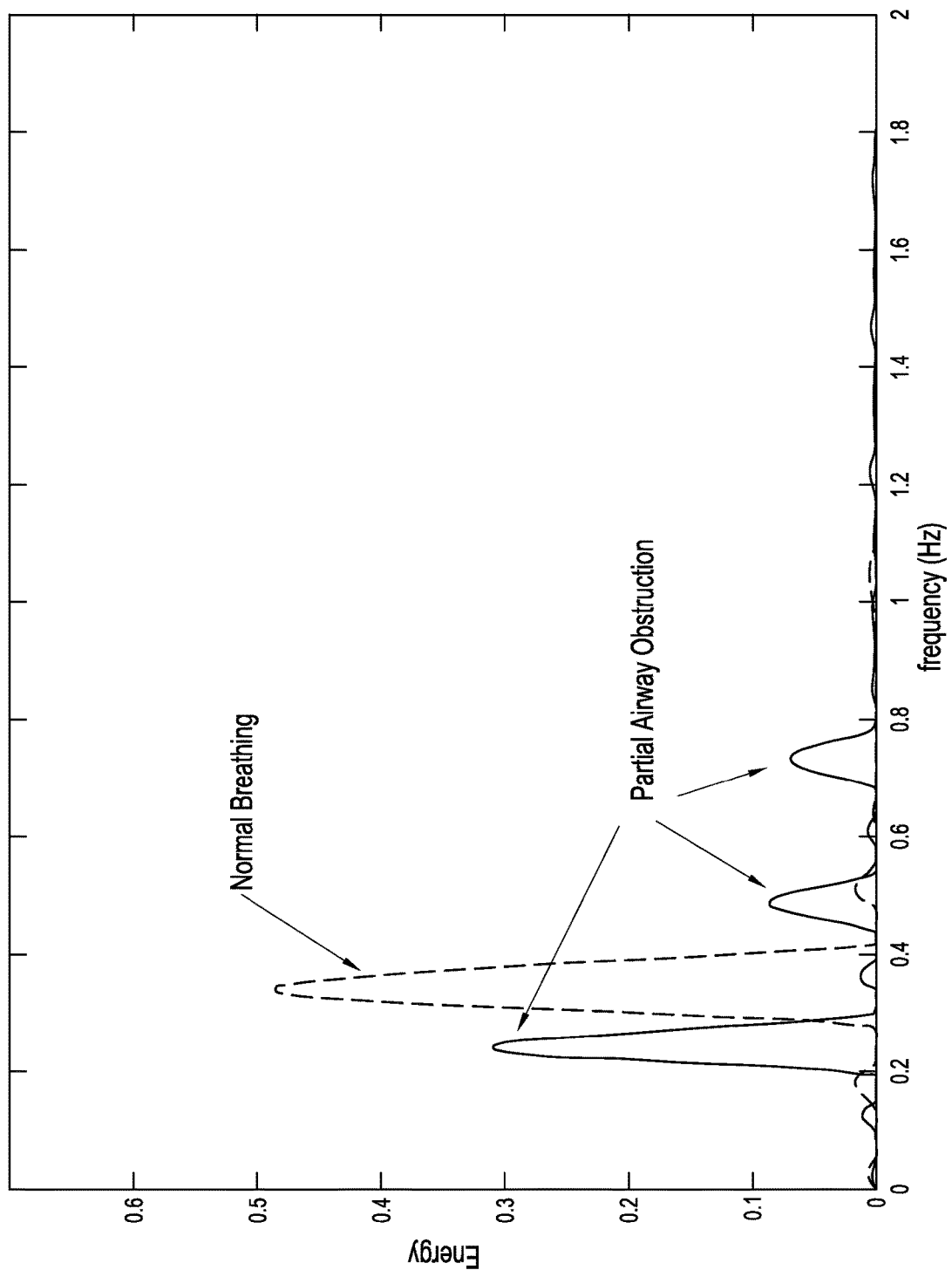
FIG. 2 is also a plot in the frequency domain of energy v. frequency for normal breathing and breathing characterized by partial airway obstruction.

In order to determine if a breath contains a partial airway obstruction, Fourier analysis is used to analyze the inspiratory flow for features specific to partial airway obstruction. Once a signal has been mapped to the frequency domain via a Fourier transform, there are many ways to represent and analyze the frequency domain information. One could analyze the direct result of the Fourier transform, which would give the amplitude of the Fourier transform's sine component (information representative of the odd component of the original signal) and the amplitude of the Fourier transform's cosine component (information representing the even component of the original signal). Alternatively, from the Fourier transform, one could construct a phase v. frequency plot and an energy v. frequency plot (energy spectrum). The phase and energy information could be used to analyze the original waveform. An alternative to the energy v. frequency plot is to construct a magnitude v. frequency plot. In the preferred embodiment an energy spectrum is used to determine the presence of partial airway obstruction. Partial airway obstructions can be detected from analysis of the energy spectrum at low frequencies, as illustrated in FIGS. 1 and 2.

In particular, energy statements involving groupings of the frequency harmonics of the Fourier transform of the flow of therapeutic gas to the patient are generated from frequency-domain considerations. This technique allows analysis of signals that might have a considerable amount of background noise. All processing and analysis is done in the frequency domain based upon observed relationships between the patient's responses and the character of the energy spectrum in the frequency domain.

Additionally, severe airway obstruction often results in a reduced peak flow-rate during inspiration, which results in a prolongation of time spent inspiring relative to expiring. This increase in inspiratory time is incorporated in the Partial Airway Obstruction Detection Algorithm.

To obtain information solely from the inspiratory phase of the respiratory cycle, Fourier analysis is performed on a waveform consisting of two inspiratory phases oppositely combined. The result is an odd function defined as $$f(-x) = -f(x) \tag{1}$$

The standard Fourier series definition is $$f(x) = \frac{A_0}{2} + \sum_{n=1}^{\infty} \left( A_n \cos \frac{n\pi x}{T} + B_n \sin \frac{n\pi x}{T} \right) \tag{2}$$

where n is the number of harmonics, $A_n$ are the harmonic cosine coefficients, $B_n$ are the harmonic sine coefficients, and T is the period of cycle. Modifying Equation (2) according to Equation (1) gives $$f(x) = \sum_{n=1}^{\infty} B_n \sin \frac{n\pi x}{T} \tag{3}$$

as all $A_n$, which represent the even part of the function, are zero.

To apply Fourier analysis to the inspiratory waveform, the algorithm of the preferred embodiment of the present invention first samples the incoming flow signal. Inspiration is then separated from expiration and manipulated as in Equation (1) to give a vector of N data points, $y=[y_1\ y_2\ \ldots\ y_N]$, that represent a single period of a cyclic function. The data is sampled evenly in time, hence $t_{j\pm 1}=\tau j$ where $\tau$ is the sampling interval between data points j=0, -1. The discrete Fourier transform of y is defined as $$Y_{k+1} = \sum_{j=0}^{N-1} y_{j+1} e^{-2\pi ijk/N} \tag{4}$$

where i is the square root of negative one and k=0, ..., N–1. Each point $Y_{k\pm i}$ of the transform has an associated frequency, $$f_{k+1} = k/\tau N \tag{5}$$

In the preferred embodiment, the fundamental frequency, k=1, is defined as $f_2=1/\tau N$ and the first harmonic frequency, k=2, is defined as $f_3=2/\tau N$.

In order to determine whether a breath is a partial airway obstruction, the relative energy of specific frequencies and groups of frequencies is analyzed. To do this the energy spectrum is calculated, $$W_{k+1} = |Y_{k+1}|^2 \tag{6}$$

and normalized such that the total energy equals one.

In the preferred embodiment, the first 13 harmonics are considered for analysis, as the relative power in the higher harmonics is minuscule. The analyzed harmonics are in the frequency range of zero to 25 Hz. The energy distribution of an inspiratory contour of a normal breath generally will have a majority of energy situated at $W_2$, which is associated with the fundamental frequency, and a small amount of energy is distributed among the harmonics. The present invention uses this characteristic of the energy spectrum as developed through Fourier analysis to posit that if the relative energy situated at a particular frequency or group of frequencies is above an empirically-observed threshold, the breath is deemed to be a partial airway obstruction.

Generally, for a normal breath the percentage of time spent inspiring is 40 percent and expiring is 60 percent. The patient 1 with a partially collapsed airway cannot achieve maximum inspiratory flow. Accordingly, the patient 1 extends the time spent inspiring relative to expiring. The time spent inspiring increases to 50 percent or more of the total breath during a partial airway obstruction.

Accordingly, the Partial Airway Obstruction Detection Algorithm first calculates an initial ratio, $I_{insp}$, which is the portion of the entire breath spent on inspiration greater than the mean (step 402). Note that bias flow has been previously removed (steps 204, 206), so the mean of the breath should be zero or very close to zero. Next, the algorithm determines the inspiratory part of the breath and constructs a waveform consisting of two inspiratory phases oppositely combined (step 404). Then, the algorithm calculates the discrete energy spectrum of the oppositely combined waveform as a function of frequency f (step 406):

$$W(f)=|FFT(\text{waveform})|^2$$

It is assumed that no significant energy is contained in the frequencies (or harmonics) above a predetermined level, preferably 13 times the fundamental frequency. Therefore, the energy spectrum is only retained, in the preferred embodiment, up to 13 times the fundamental frequency (step 408). Next, the algorithm normalizes the energy spectrum such that the total energy equals one (step 410):

$$\text{normalized energy spectrum}=W(f)/\Sigma W(F)$$

This calculation is done so that all breaths will be analyzed the same, even though each breath may differ from another breath in duration, tidal volume, and maximum flow.

Next, the algorithm groups energies corresponding to different harmonic frequencies into information-bearing values (step 412). These information-bearing values are compared to threshold values that are calculated in accordance with the percentage of the breath that is spend on inspiration (step 414). The information-bearing values and the threshold values are determined empirically.

In the preferred embodiment, four information-bearing values are used: $W_{first}$, $W_{second}$, $W_{freq}$, and $W_{high\_freq}$, as follows:

$$W_{first} = W_3$$

$$W_{second} = W_4$$

$$W_{freq} = \sum_{k=2}^{14} W_{k+1}$$

$$W_{high\_freq} = \sum_{k=6}^{14} W_{k+1}$$

According, $W_{first}$ corresponds to the energy in the first harmonic, $W_{second}$ corresponds to the energy in the second harmonic, $W_{freq}$ corresponds to the energy in the first 13 harmonics, and $W_{high\_freq}$ corresponds to the energy in the harmonics five through 13. Other information-bearing values can be obtained from the energies corresponding to different harmonic frequencies using other mathematical operations.

In the preferred embodiment, two thresholds are used, $T_{freq}$ and $T_{high\_freq}$. These values vary depending on the value of $I_{insp}$, the percentage of the breath spend inspiring (calculated at step 402) and have been determined empirically to be:

| Threshold | $I_{insp}$ | Value |
|---|---|---|
| $T_{freq}$ | $I_{insp} \leq 40$ | 0.15 |
| $T_{freq}$ | $40 < I_{insp} 50$ | $-0.005 \times I_{insp} + 0.35$ |
| $T_{freq}$ | $I_{insp} \geq 50$ | 0.1 |
| $T_{high\_freq}$ | $I_{insp} \leq 40$ | 0.03 |
| $T_{high\_freq}$ | $40 < I_{insp} 60$ | $-0.001 \times I_{insp} + 0.07$ |
| $T_{high\_freq}$ | $I_{insp} \geq 60$ | 0.01 |

Using these empirically-determined values, the algorithm computes the information-bearing summations to the thresholds. If $W_{second}$ is greater than or equal to 0.1 (step 416), the breath is a partial airway obstruction (step 418). If $W_{first}$ is greater than or equal to 0.02, $W_{second}$ is greater than or equal to 0.02, and $W_{freq}$ is greater than or equal to 0.12 (step 420), the breath is a partial airway obstruction (step 422). If the sum of $W_{first}$ and $W_{second}$ is greater than or equal to 0.06 and $W_{freq}$ is greater than or equal to 0.12 (step 424), the breath is a partial airway obstruction (step 426). If the sum of $W_{first}$ and $W_{second}$ is greater than or equal to 0.07 and $W_{freq}$ is greater than or equal to 0.11 (step 428), the breath is a partial airway obstruction (step 430). If $W_{freq}$ is greater than or equal to $T_{freq}$ (step 432), the breath is a partial airway obstruction (step 434). If $W_{high\_freq}$ is greater than or equal to $T_{high\_freq}$ (step 436), the breath is a partial airway obstruction (step 438). If none of these comparisons is true, the breath is normal (step 440).

Apnea Detection Algorithm

Figure 7:
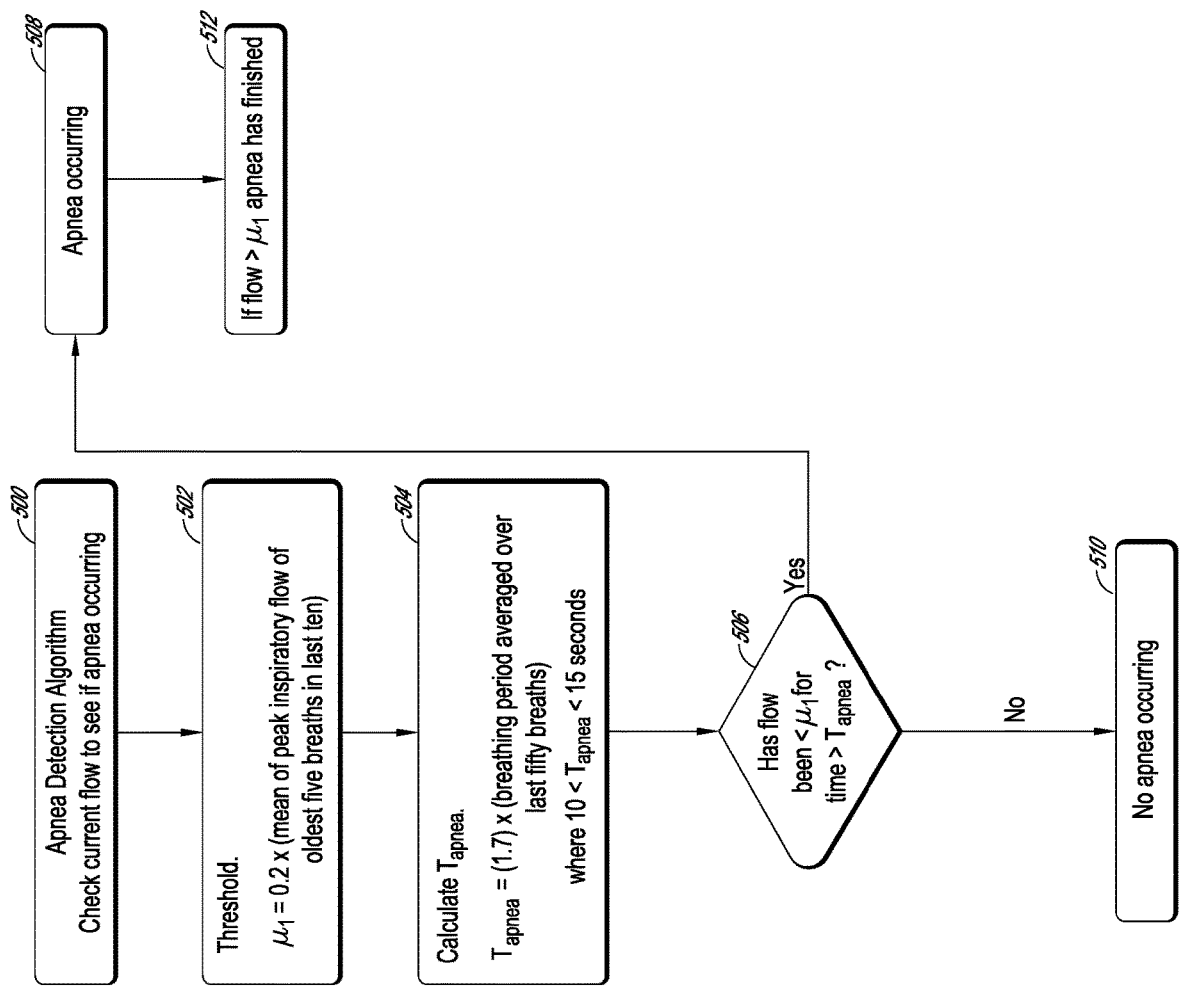
FIG. 7 is a block diagram of the Apnea Detection Algorithm of the preferred embodiment of the present invention.

The Apnea Detection Algorithm (step 500) is diagramed in FIG. 7. In order to detect an apnea (cessation of flow), the controller 9 compares the incoming flow data (minus bias flow) with a threshold, determined by the previous peak inspiratory flow. The Breath Detection Algorithm (step 300) had previously stored the maximum or peak inspiratory flow, not part of a hypopnea. The Apnea Detection Algorithm calculates the threshold, $\mu_1$, as 20 percent of the average peak inspiratory flow of the oldest five breaths of the last ten breaths (step 502). The algorithm then calculates $T_{apnea}$ (step 504):

$$T_{apnea}=1.7\times(\text{breathing period averaged over last 50 breaths})$$

$T_{apnea}$, however, must be between ten and fifteen seconds.

If the incoming flow is less than the threshold, $\mu_1$, an apnea may be occurring. If this condition is met for time greater than $T_{apnea}$ (step 506), then an apnea is occurring (step 508), otherwise, no apnea occurred (step 510). If an apnea is occurring, the algorithm checks to see when the flow has increased to more than the threshold, $\mu_1$ (step 512), indicating that the apnea has finished.

Hypopnea Detection Algorithm

Figure 8:
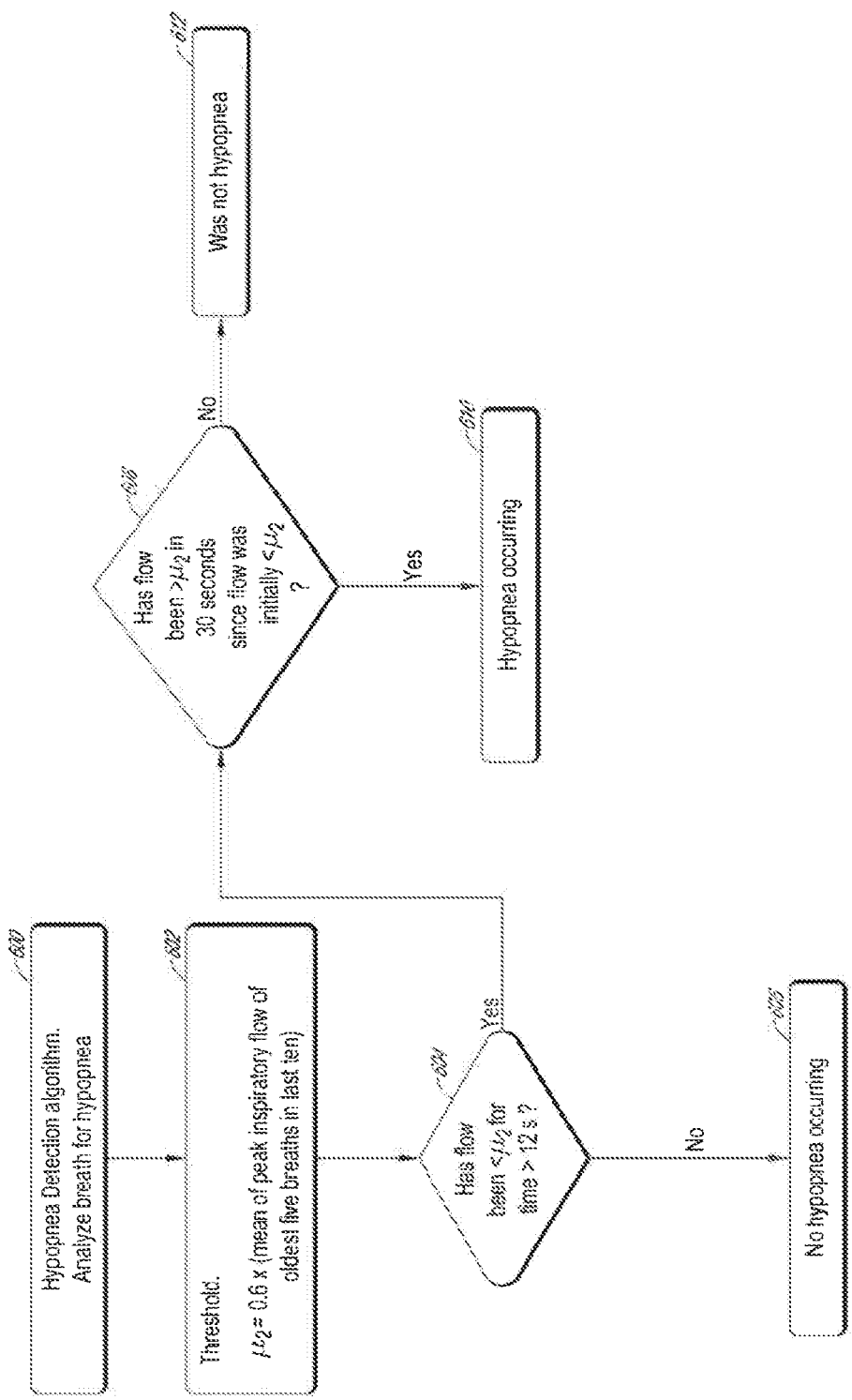
FIG. 8 is a block diagram of the Hypopnea Detection Algorithm of the preferred embodiment of the present invention.
Figure 9A:
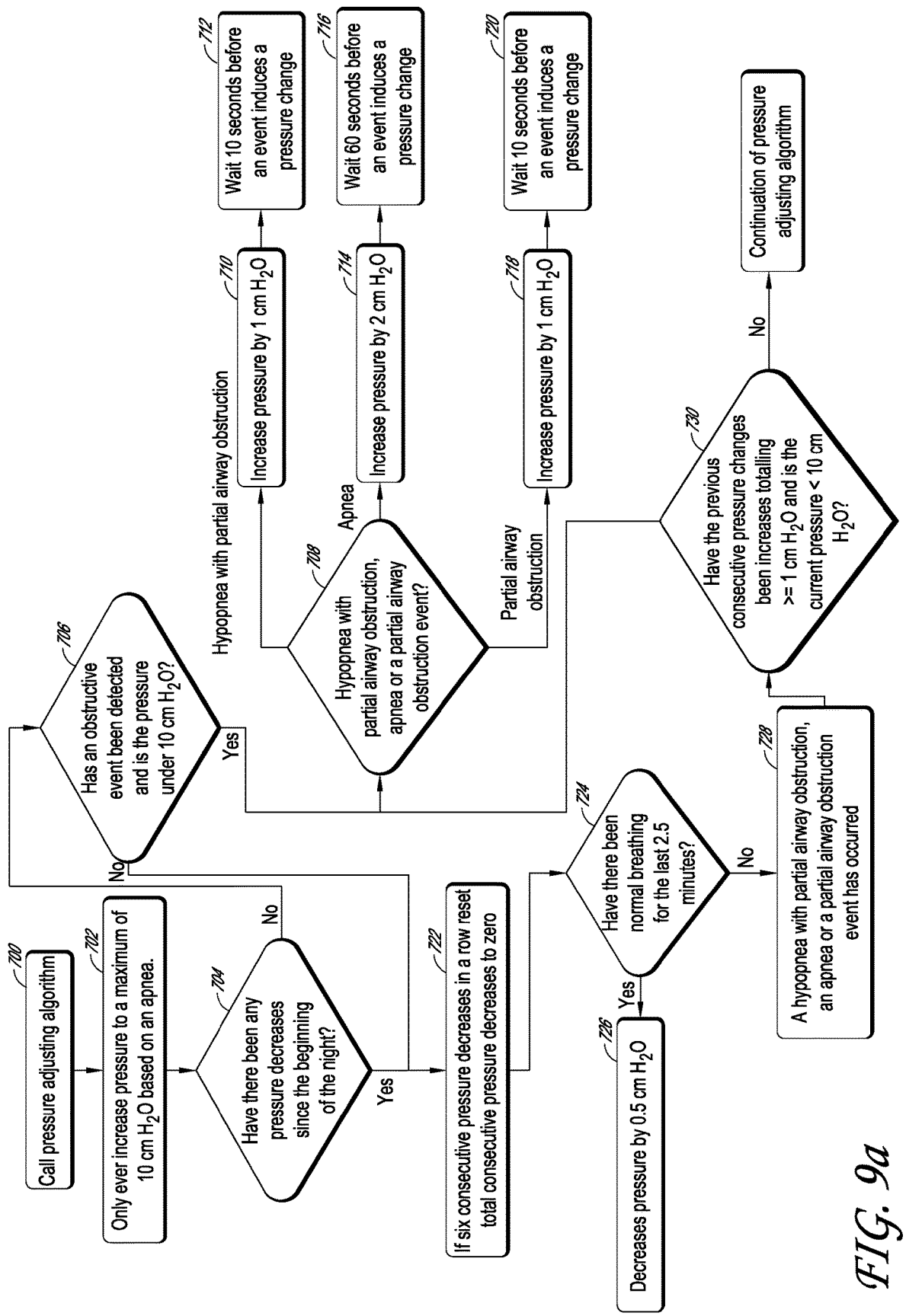
FIGS. 9a, 9b, 9c, and 9d are block diagrams of the Pressure Adjusting Algorithm of the preferred embodiment of the present invention.
Figure 9B:
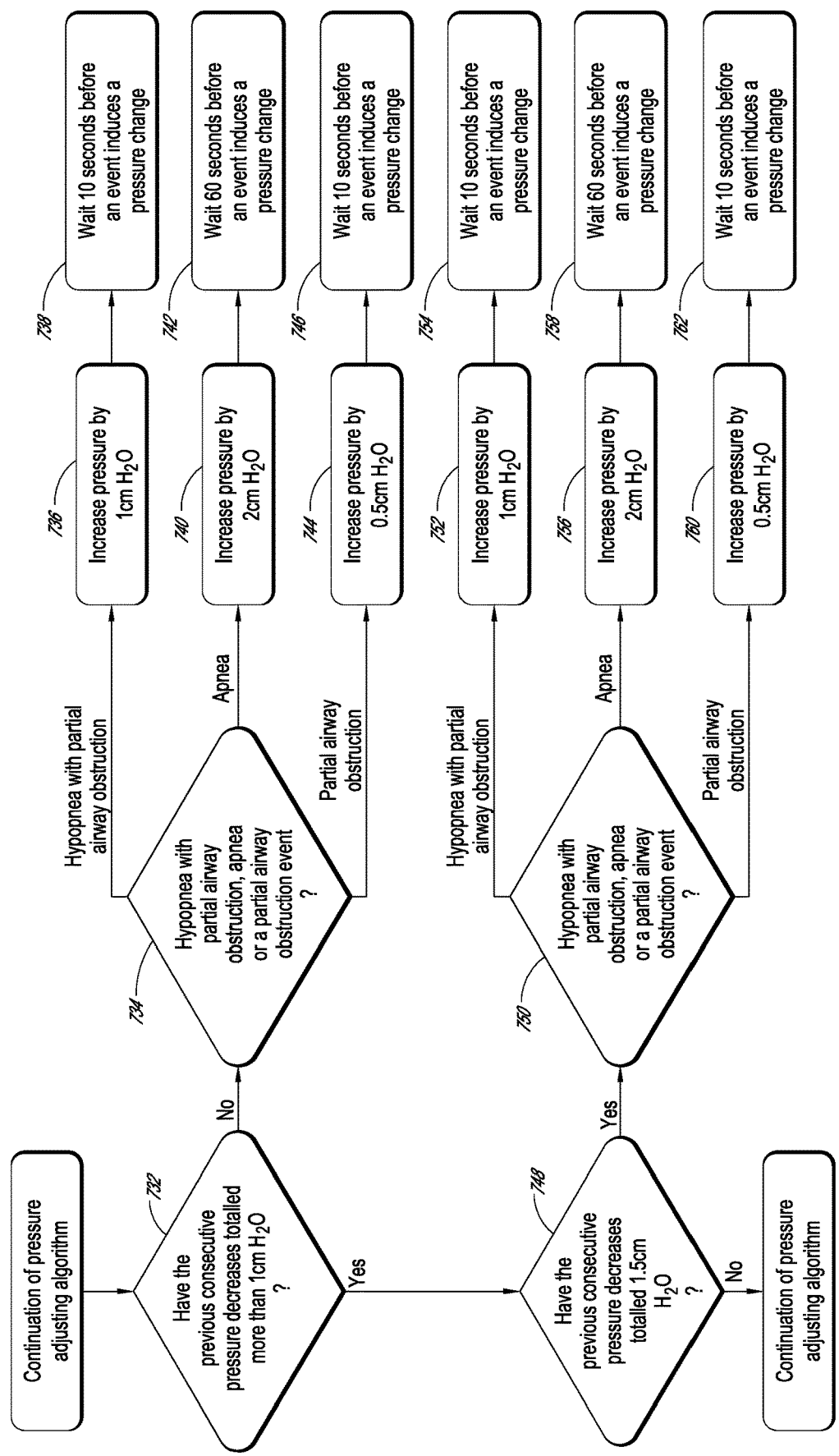
Figure 9C:
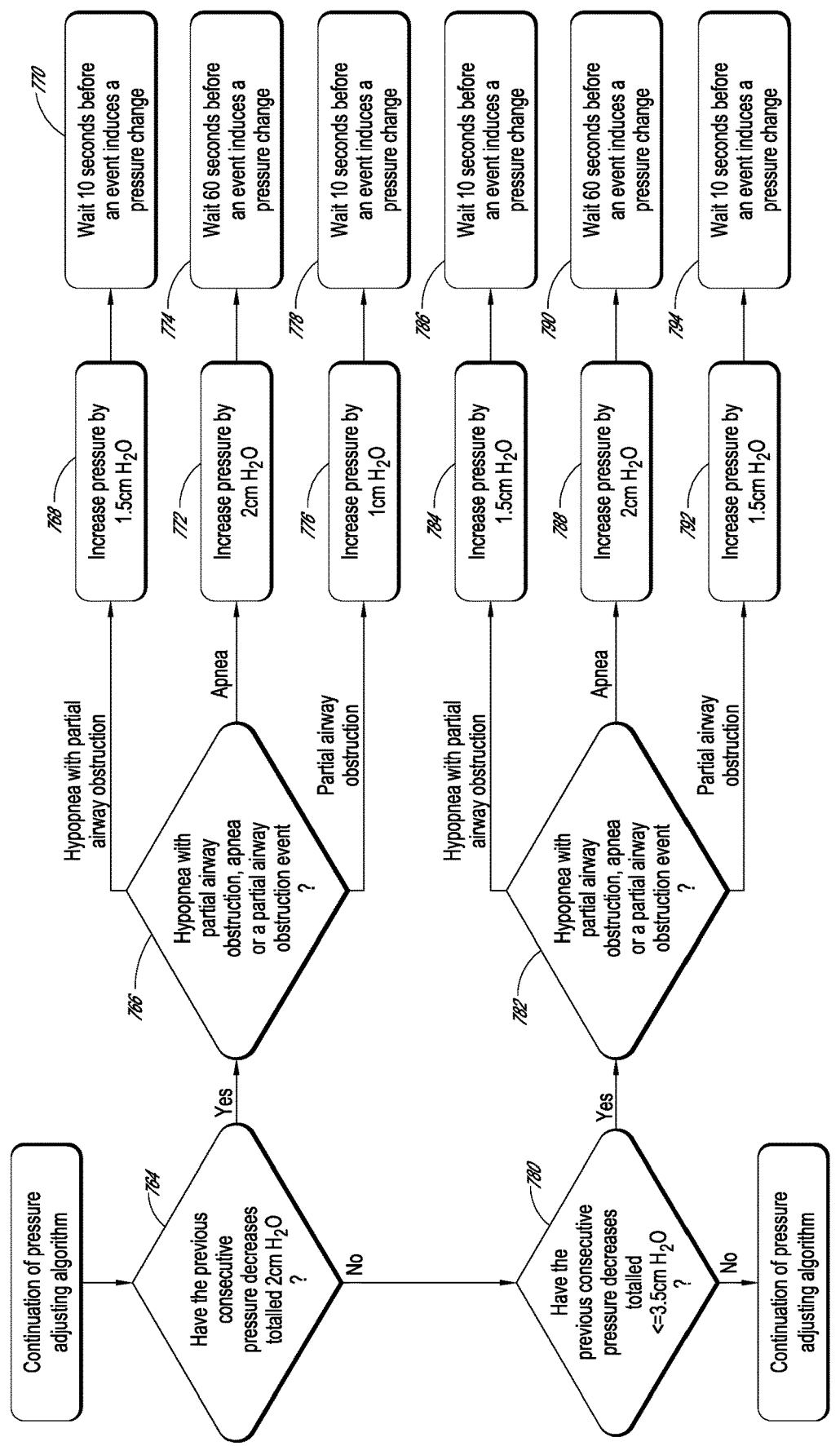
Figure 9D:
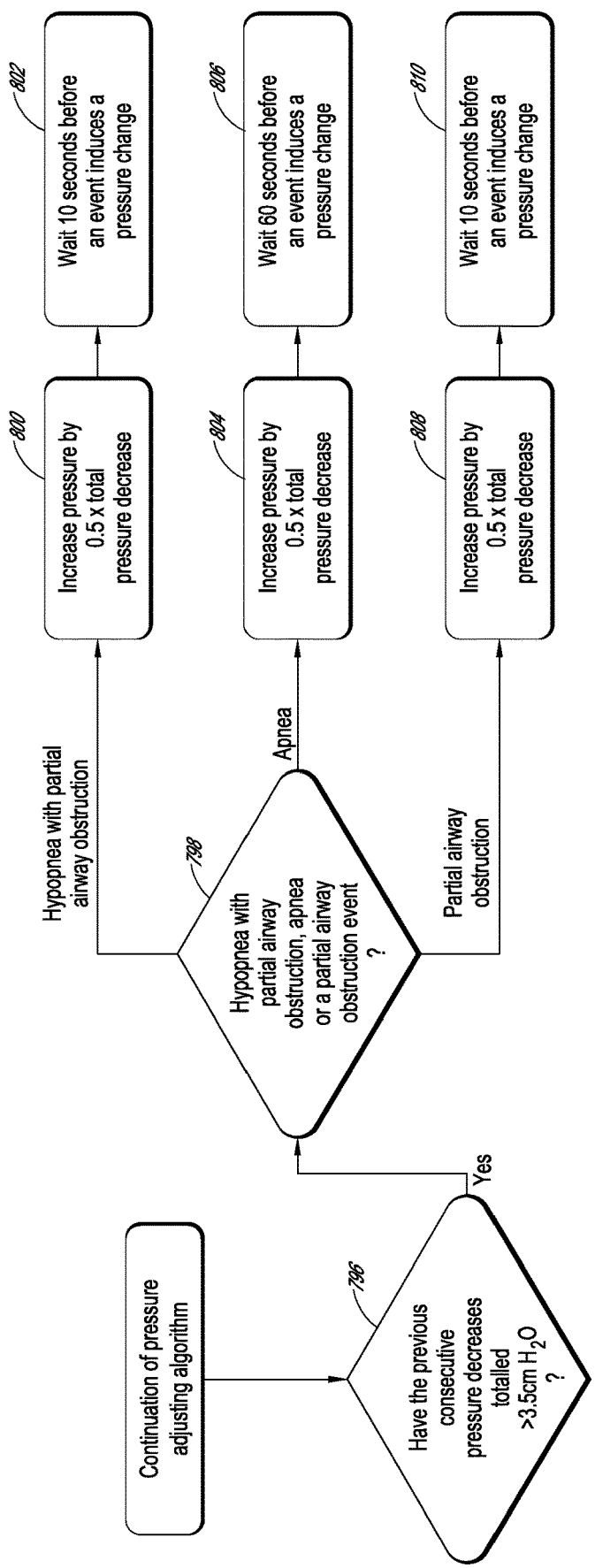

In order to detect a hypopnea (reduction of flow), the Hypopnea Detection Algorithm (step 600), as diagramed in FIG. 8, compares the stored breath with a threshold, $\mu_2$, determined by the previous peak inspiratory flow (step 602). Similar to the Apnea Detection Algorithm (step 500), the threshold, $\mu_2$, is calculated from the peak inspiratory flow for the oldest five breaths of the last ten that did not constitute part of a hypopnea. The threshold ($\mu_2$) is then taken as 60 percent of the average peak inspiratory flow of the oldest five breaths (step 602).

If incoming flow is less than the threshold ($\mu_2$), for a period of time greater than 12 seconds (step 604), then a possible hypopnea has occurred; otherwise, no hypopnea is occurring (step 606). For the event to be classified as a hypopnea, there must be an increase in flow such that flow is greater than $\mu_2$ within 30 seconds since the flow was less than $\mu_2$ (step 608). If this increase in flow is detected, a hypopnea occurred (step 610); otherwise, the event was not a hypopnea (step 612).

Pressure Adjusting Algorithm

If an apnea was detected during the Apnea Detection Algorithm (step 500), the Pressure Adjusting Algorithm (step 700) is called. Also, if a hypopnea was detected during the Hypopnea Detection Algorithm (step 600), and there were partial airway obstruction breaths in the hypopnea (step 228), or if there was no hypopnea but the current breath and two previous breaths were partial airway obstructions (steps 226, 232, 234), the Pressure Adjusting (step 700)

algorithm is called. If there was no hypopnea, and either the current breath does not show a partial airway obstruction or the previous two breaths did not show a partial airway obstruction, but is has been 2.5 minutes since the last partial airway obstruction (steps 226, 232, 234, 224), the Pressure Adjusting Algorithm is called. Also, if there was a hypopnea, but without any partial airway obstruction breaths, and it has been longer than a predetermined period since the last partial airway obstruction event or apnea, preferably 2.5 minutes (steps 226, 228, and 230), the Pressure Adjusting Algorithm (step 700) is called. The Pressure Adjusting Algorithm is diagramed in FIGS. 9a through 9d.

The Pressure Adjusting Algorithm (step 700) determines whether to adjust the pressure and by how much, in order to control the therapeutic pressure delivered to the patient. As an initial rule of the preferred embodiment, this algorithm will only increase pressure to a maximum of 10 cm $H_2O$ on an event classified as an apnea (step 702).

The algorithm first checks to determine if there have been any pressure decreases since the beginning of the period of sleep (step 704). If there have not been any such decreases, the algorithm determines if an obstructive event of any sort has been detected and whether the pressure is under a predetermined maximum, preferably ten cm $H_2O$ (step 706). If these conditions are met, the algorithm determines whether the obstructive event was a partial airway obstruction, an apnea, or a hypopnea with a partial airway obstruction (step 708). In the event of a hypopnea with a partial airway obstruction, the controller 9 increases pressure by one cm $H_2O$ (step 710) and waits ten seconds before allowing another pressure change (step 712). If the event was an apnea, the controller 9 increases pressure by two cm $H_2O$ (step 714) and waits 60 seconds before allowing another pressure change (step 716). If the event was a partial airway obstruction, the controller 9 increases pressure by one cm $H_2O$ (step 718) and waits ten seconds before allowing another pressure change (step 720).

If there have been previous pressure decreases since the beginning of the period of sleep (step 704), or if the conditions of a detected obstructive event and the pressure being less than ten cm $H_2O$ have not been met (step 706), the algorithm determines if there have been six consecutive pressure decreases. If so, total consecutive pressure-decrease counter 130 is reset to zero (step 722).

The algorithm next determines if there has been normal breathing for a predetermined period of time, preferably 2.5 minutes (step 724). If so, the controller 9 decreases the pressure by 0.5 cm $H_2O$ (step 726) (and increments pressure-decrease counter 130 by one).

If there has not been normal breathing for the predetermined period of time (step 724), then either a partial airway obstruction, an apnea, or a hypopnea with partial airway obstruction has occurred (step 728). The next step depends on the previous pressure changes. If the previous consecutive pressure changes have been increases totaling greater than or equal to a total of one cm $H_2O$, and the current pressure is less than ten cm $H_2O$ (step 730), the algorithm proceeds to step 708 as described above. If not, the controller 9 proceeds to increase the pressure by an amount depending on the nature of the obstructive event and the amount of previous pressure decreases, as diagramed in FIGS. 9b, 9c, and 9d.

If the total previous pressure decreases were more than one cm $H_2O$ (step 732), the algorithm determines if the obstructive event was a partial airway obstruction, an apnea, or a hypopnea with partial airway obstruction (step 734). In the event of a hypopnea with a partial airway obstruction, the controller 9 increases pressure by one cm $H_2O$ (step 736) and waits ten seconds before allowing another pressure change (step 738). If the event was an apnea, the controller 9 increases pressure by two cm $H_2O$ (step 740) and waits 60 seconds before allowing another pressure change (step 742). If the event was a partial airway obstruction, the controller 9 increases pressure by 0.5 cm $H_2O$ (step 744) and waits ten seconds before allowing another pressure change (step 746).

If the previous pressure decreases were more than one cm $H_2O$ but not more than 1.5 cm $H_2O$ (step 748), the algorithm determines if the obstructive event was a partial airway obstruction, an apnea, or a hypopnea with partial airway obstruction (step 750). In the event of a hypopnea with partial airway obstruction, the controller 9 increases pressure by one cm $H_2O$ (step 752) and waits ten seconds before allowing another pressure change (step 754). If the event was an apnea, the controller 9 increases pressure by two cm $H_2O$ (step 756) and waits 60 seconds before allowing another pressure change (step 758). If the event was a partial airway obstruction, the controller 9 increases pressure by 0.5 cm $H_2O$ (step 760) and waits ten seconds before allowing another pressure change (step 762).

If the previous pressure decreases were more than 1.5 cm $H_2O$ but not more than two cm $H_2O$ (step 764) (FIG. 9c), the algorithm determines if the obstructive event was a partial airway obstruction, an apnea, or a hypopnea with partial airway obstruction (step 766). In the event of a hypopnea with partial airway obstruction, the controller 9 increases pressure by 1.5 cm $H_2O$ (step 768) and waits ten seconds before allowing another pressure change (step 770). If the event was an apnea, the controller 9 increases pressure by two cm $H_2O$ (step 772) and waits 60 seconds before allowing another pressure change (step 774). If the event was a partial airway obstruction, the controller 9 increases pressure by one cm $H_2O$ (step 776) and waits ten seconds before allowing another pressure change (step 778).

If the previous pressure decreases were more than two cm $H_2O$ but less than or equal to 3.5 cm $H_2O$ (step 780), the algorithm determines if the obstructive event was a partial airway obstruction, an apnea, or a hypopnea with partial airway obstruction (step 782). In the event of a hypopnea with partial airway obstruction, the controller 9 increases pressure by 1.5 cm $H_2O$ (step 784) and waits ten seconds before allowing another pressure change (step 754). If the event was an apnea, the controller 9 increases pressure by two cm $H_2O$ (step 788) and waits 60 seconds before allowing another pressure change (step 790). If the event was a partial airway obstruction, the controller 9 increases pressure by 1.5 cm $H_2O$ (step 792) and waits ten seconds before allowing another pressure change (step 794).

If the previous pressure decreases were more than 3.5 cm $H_2O$ (step 796), the algorithm determines if the obstructive event was a partial airway obstruction, an apnea, or a hypopnea with partial airway obstruction (step 798). In the event of a hypopnea with partial airway obstruction, the controller 9 increases pressure by one-half the total pressure decrease (step 800) and waits ten seconds before allowing another pressure change (step 802). If the event was an apnea, the controller 9 increases pressure by one-half the total pressure decrease (step 804) and waits 60 seconds before allowing another pressure change (step 806). If the event was a partial airway obstruction, the controller 9 increases pressure by one-half the total pressure decrease (step 808) and waits ten seconds before allowing another pressure change (step 810).

While preferred embodiments of the present invention are shown and described, it is envisioned that those skilled in the art may devise various modifications of the present invention without departing from the spirit and scope of the appended claims.

What is claimed is:

1. A method of controlling positive airway pressure therapy, comprising:
providing gas to an airway of a patient at a pressure;
determining a flow of the gas provided to the airway of the patient;
detecting hypopnea based in part on determining that the flow falls below a hypopnea entry flow threshold and that the flow subsequently exceeds a hypopnea exit flow threshold within a maximum time duration, wherein the hypopnea entry and hypopnea exit flow thresholds are based at least in part on a plurality of previous flow values of the gas provided to the airway of the patient; and
increasing the pressure of the gas in response to detecting the hypopnea, the increasing comprising, in response to detecting that the hypopnea was preceded by a pressure decrease:
increasing the pressure of the gas by a first magnitude in response to determining that a magnitude of the pressure decrease does not satisfy a threshold; and
increasing the pressure of the gas by a second magnitude in response to determining that the magnitude of the pressure decrease satisfies the threshold, the second magnitude being larger than the first magnitude, and the second magnitude being proportional to the magnitude of the pressure decrease.

2. The method of claim 1, further comprising detecting occurrence of a current breath in the flow of gas, wherein determining that the flow falls below the hypopnea entry flow threshold comprises determining that a flow value of the current breath falls below the hypopnea entry flow threshold.

3. The method of claim 1, wherein detecting the hypopnea further comprises determining that the flow does not exceed a minimum flow threshold for a minimum predetermined duration of time, the minimum flow threshold based at least in part on an average of flow values of a plurality of previous breaths, the average excluding one or more most recent breaths of the plurality of previous breaths.

4. The method of claim 1, wherein the flow falling below the hypopnea entry flow threshold indicates a potential start of hypopnea, and the flow exceeding the hypopnea exit flow threshold indicates a potential end of hypopnea, and wherein the detection of the hypopnea further requires that a time duration between the potential start of hypopnea and the potential end of hypopnea complies with a minimum time requirement.

5. The method of claim 4, wherein detecting the hypopnea further comprises requiring flow values of current breaths between the potential start of hypopnea and the potential end of hypopnea to fall below a minimum flow threshold for at least the minimum time requirement, the minimum flow threshold based at least in part on an average of flow values of a plurality of previous breaths, the average excluding one or more most recent breaths of the plurality of previous breaths.

6. The method of claim 1, wherein the magnitude of the preceding pressure decrease comprises a sum of a plurality of preceding pressure decreases.

7. A positive airway pressure therapy apparatus comprising:
a blower configured to provide a flow of gas to an airway of a patient at a pressure;
a sensor configured to monitor the flow of the gas; and
a controller configured to:
determine the flow of the gas based on an output of the sensor;
detect hypopnea in response to a determination that the flow falls below a hypopnea entry flow threshold and that the flow subsequently exceeds a hypopnea exit flow threshold within a maximum time duration, wherein the hypopnea entry and hypopnea exit flow thresholds are based at least in part on a plurality of previous flow values of the gas provided to the airway of the patient; and
cause increase of the pressure of the gas in response to the detection of the hypopnea, the controller further configured to, in response to a detection that the hypopnea has been preceded by a pressure decrease:
cause increase of the pressure of the gas by a first magnitude in response to a determination that a magnitude of the pressure decrease does not satisfy a threshold; and
cause increase of the pressure of the gas by a second magnitude in response to a determination that the magnitude of the pressure decrease satisfies the threshold, the second magnitude being larger than the first magnitude, and the second magnitude being proportional to the magnitude of the pressure decrease.

8. The apparatus of claim 7, wherein the controller is further configured to:
determine a total flow of the gas provided to the airway of the patient;
determine a flow due to one or more leaks in a flow path of the gas; and
subtract the flow due to one or more leaks from the total flow.

9. The apparatus of claim 7, wherein the hypopnea entry and hypopnea exit flow thresholds are determined based at least in part on an average of flow values of a plurality of previous breaths outside the hypopnea, the average excluding one or more most recent breaths of the plurality of previous breaths.

10. The apparatus of claim 9, wherein the hypopnea entry and hypopnea exit flow thresholds comprise a fraction of an average of the flow values of a plurality of previous breaths, the average excluding one or more most recent breaths of the plurality of previous breaths.

11. The apparatus of claim 7, wherein the controller is further configured to detect occurrence of a current breath in the flow of gas, and wherein the determination that the flow falls below the hypopnea entry flow threshold comprises a determination that a flow value of the current breath falls below the hypopnea entry flow threshold.

12. The apparatus of claim 7, wherein the controller is further configured to detect hypopnea based on a determination that the flow does not exceed a minimum flow threshold for a minimum predetermined duration of time, the minimum flow threshold based at least in part on an average of flow values of a plurality of previous breaths, the average excluding one or more most recent breaths of the plurality of previous breaths.

13. The apparatus of claim 7, wherein the determination that the flow falls below the hypopnea entry flow threshold indicates a potential start of hypopnea, and the determination that the flow exceeds the hypopnea exit flow threshold indicates a potential end of hypopnea, and wherein the detection of the hypopnea further requires that a time duration between the potential start of hypopnea and the potential end of hypopnea complies with a minimum time requirement.

14. The apparatus of claim 13, wherein the detection of the hypopnea further requires that flow values of current breaths between the potential start of hypopnea and the potential end of hypopnea fall below a minimum flow threshold for at least the minimum time requirement, the minimum flow threshold based at least in part on an average of flow values of a plurality of previous breaths, the average excluding one or more most recent breaths of the plurality of previous breaths.

15. The apparatus of claim 7, wherein the controller is further configured to cause increase of the pressure of the gas based on a current pressure level.

16. The apparatus of claim 7, wherein the magnitude of the preceding pressure decrease comprises a sum of a plurality of preceding pressure decreases.

17. A positive airway pressure therapy apparatus comprising:
a blower configured to provide a flow of gas to an airway of a patient at a pressure;
a sensor configured to monitor the flow of the gas; and
a controller configured to:
determine the flow of the gas based on an output of the sensor;
detect hypopnea in response to a determination that the flow falls below a hypopnea entry flow threshold and that the flow subsequently exceeds a hypopnea exit flow threshold within a maximum time duration, wherein the hypopnea entry and hypopnea exit flow thresholds are based at least in part on a plurality of previous flow values of the gas provided to the airway of the patient; and
in response to the detection of the hypopnea and a determination that the hypopnea was preceded by a pressure decrease:
cause increase of the pressure of gas by a preset pressure increase or a pressure increase determined based on a magnitude of the pressure decrease, the preset pressure increase being smaller than the pressure increase determined based on the magnitude of the pressure decrease, wherein a determination of whether to increase the pressure by the preset pressure increase or the pressure increase determined based on the magnitude of the pressure decrease is based on the magnitude of the pressure decrease.

18. The apparatus of claim 17, wherein the pressure increase determined based on the magnitude of the pressure decrease is one-half of the magnitude of the pressure decrease.

19. The apparatus of claim 17, wherein the hypopnea entry and hypopnea exit flow thresholds are determined based at least in part on an average of flow values of a plurality of previous breaths outside the hypopnea, the average excluding one or more most recent breaths of the plurality of previous breaths.

20. The apparatus of claim 19, wherein the hypopnea entry and hypopnea exit flow thresholds comprise a fraction of an average of the flow values of a plurality of previous breaths, the average excluding one or more most recent breaths of the plurality of previous breaths.

21. The apparatus of claim 17, wherein the controller is further configured to detect occurrence of a current breath in the flow of gas, and wherein the determination that the flow falls below the hypopnea entry flow threshold comprises a determination that a flow value of the current breath falls below the hypopnea entry flow threshold.

22. The apparatus of claim 17, wherein the controller is further configured to detect hypopnea based on a determination that the flow does not exceed a minimum flow threshold for a minimum predetermined duration of time, the minimum flow threshold based at least in part on an average of flow values of a plurality of previous breaths, the average excluding one or more most recent breaths of the plurality of previous breaths.

23. The apparatus of claim 17, wherein the determination that the flow falls below the hypopnea entry flow threshold indicates a potential start of hypopnea, and the determination that the flow exceeds the hypopnea exit flow threshold indicates a potential end of hypopnea, and wherein the detection of the hypopnea further requires that a time duration between the potential start of hypopnea and the potential end of hypopnea complies with a minimum time requirement.

24. The apparatus of claim 23, wherein the detection of the hypopnea further requires that flow values of current breaths between the potential start of hypopnea and the potential end of hypopnea fall below a minimum flow threshold for at least the minimum time requirement, the minimum flow threshold based at least in part on an average of flow values of a plurality of previous breaths, the average excluding one or more most recent breaths of the plurality of previous breaths.

25. The apparatus of claim 17, wherein the controller is further configured to cause increase of the pressure of the gas based on a current pressure level.

26. The apparatus of claim 17, wherein the magnitude of the pressure decrease comprises a sum of a plurality of preceding pressure decreases.

* * * * *

UNITED STATES PATENT AND TRADEMARK OFFICE
CERTIFICATE OF CORRECTION

PATENT NO. : 11,129,949 B2
APPLICATION NO. : 14/864378
DATED : September 28, 2021
INVENTOR(S) : Gradon et al.

Page 1 of 1

It is certified that error appears in the above-identified patent and that said Letters Patent is hereby corrected as shown below:

In the Specification

In Column 8, Line 19, delete "$t_{j\pm1}$" and insert --$t_{j+1}$--.

In Column 8, Line 20, delete "j=0, -1." and insert --j=0, ... -1.--.

In Column 8, Line 29, delete "$Y_{k\pm i}$" and insert --$Y_{k+i}$--.

In Column 10, Line 20, delete "threshold," and insert --threshold, µ1,--.

In the Claims

In Column 13, Line 62, Claim 6, delete "preceding pressure" and insert --pressure--.

In Column 15, Line 16, Claim 16, delete "preceding pressure" and insert --pressure--.

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*